United States Patent
Ambrosina et al.

(10) Patent No.: US 11,285,262 B2
(45) Date of Patent: Mar. 29, 2022

(54) FLUID FLOW MEASUREMENT AND CONTROL

(71) Applicant: Ivenix, Inc., North Andover, MA (US)

(72) Inventors: Jesse E. Ambrosina, Topsfield, MA (US); Benjamin G. Powers, Portsmouth, NH (US); Michael J. Scarsella, Merrimac, MA (US)

(73) Assignee: Ivenix, Inc., North Andover, MA (US)

( * ) Notice: Subject to any disclaimer, the term of this patent is extended or adjusted under 35 U.S.C. 154(b) by 63 days.

(21) Appl. No.: 16/594,441

(22) Filed: Oct. 7, 2019

(65) Prior Publication Data
US 2020/0038585 A1 Feb. 6, 2020

Related U.S. Application Data

(63) Continuation-in-part of application No. 15/468,546, filed on Mar. 24, 2017, now Pat. No. 10,444,770, (Continued)

(51) Int. Cl.
*A61M 5/168* (2006.01)
*G05D 7/06* (2006.01)
(Continued)

(52) U.S. Cl.
CPC .... *A61M 5/16809* (2013.01); *A61M 5/14586* (2013.01); *A61M 5/16827* (2013.01); *A61M 5/16881* (2013.01); *A61M 5/16886* (2013.01); *A61M 5/385* (2013.01); *B01D 19/0031* (2013.01); *B01D 19/0063* (2013.01);
(Continued)

(58) Field of Classification Search
None
See application file for complete search history.

(56) References Cited

U.S. PATENT DOCUMENTS 4,337,639 A 7/1982 Jackson
4,976,162 A * 12/1990 Kamen ............ A61M 5/16809
73/865.9
(Continued)

FOREIGN PATENT DOCUMENTS

CN 102607889 A * 7/2012
WO 20090094590 A2 7/2009

OTHER PUBLICATIONS

Derwent Abstract Translation of Attached CN Patent Publication 102607889A, 2012. (Year: 2012).*
(Continued)

*Primary Examiner* — Ryan D. Coyer
(74) *Attorney, Agent, or Firm* — Armis IP Law, LLC

(57) ABSTRACT

A controller in a fluid delivery system controls magnitudes of pressure in a first volume and a second volume. The first volume is of a known magnitude. The second volume is of an unknown magnitude and varies. The controller estimates a temperature of gas in the first volume and a temperature of gas in the second volume based on measurements of pressure in the first volume and measurements of pressure in the second volume. The controller then calculates a magnitude of the second volume based on measured pressures of the gases and estimated temperatures of gases in the first volume and the second volume.

28 Claims, 18 Drawing Sheets

1700

DRAW FLUID INTO A CHAMBER OF A DIAPHRAGM PUMP — 1710

APPLY PRESSURE TO THE CHAMBER OF THE DIAPHRAGM PUMP TO OUTPUT THE FLUID IN THE CHAMBER OF THE DIAPHRAGM PUMP DOWNSTREAM THROUGH A FLUID CONDUIT TO A POSITIVE DISAPLCEMENT PUMP — 1720

DURING APPLICATION OF THE PRESSURE TO THE CHAMBER AND OUTPUTTING THE FLUID IN THE CHAMBER DOWNSTREAM, ACTIVATE OPERATION OF THE POSITIVE DISPLACEMENT PUMP TO PUMP THE FLUID FROM THE POSITIVE DISPLACEMENT PUMP TO A RECIPIENT — 1730

Related U.S. Application Data which is a continuation-in-part of application No. 14/171,433, filed on Feb. 3, 2014, now Pat. No. 9,616,172.

(60) Provisional application No. 61/761,109, filed on Feb. 5, 2013.

(51) Int. Cl.
  B01D 19/00 (2006.01)
  A61M 5/145 (2006.01)
  A61M 5/38 (2006.01)

(52) U.S. Cl.
  CPC ....... G05D 7/0682 (2013.01); *A61M 2205/12* (2013.01); *A61M 2205/3389* (2013.01)

(56) References Cited

U.S. PATENT DOCUMENTS

| | | | |
|---|---|---|---|
| 5,421,208 A | 6/1995 | Packard et al. | |
| 5,474,683 A | 12/1995 | Bryant et al. | |
| 6,604,908 B1* | 8/2003 | Bryant | A61M 1/367 417/26 |
| 7,654,982 B2 | 2/2010 | Carlisle et al. | |
| 8,594,954 B2 | 11/2013 | Macron et al. | |
| 2002/0182090 A1 | 12/2002 | Gray et al. | |
| 2005/0177821 A1* | 8/2005 | Ogata | G06F 11/3612 717/148 |
| 2005/0209563 A1* | 9/2005 | Hopping | A61M 1/281 604/151 |
| 2007/0264130 A1 | 11/2007 | Mallett | |
| 2009/0131863 A1 | 5/2009 | Carlisle et al. | |
| 2010/0040483 A1 | 2/2010 | Berger et al. | |
| 2011/0004143 A1* | 1/2011 | Beiriger | G16H 40/63 604/6.11 |
| 2011/0028937 A1 | 2/2011 | Powers et al. | |
| 2011/0168270 A1 | 7/2011 | Carlisle et al. | |
| 2011/0218486 A1 | 9/2011 | Huitt et al. | |
| 2011/0254686 A1 | 10/2011 | Kalpin | |
| 2012/0123322 A1 | 5/2012 | Scarpaci et al. | |
| 2012/0312726 A1 | 12/2012 | Gagel | |
| 2013/0045115 A1* | 2/2013 | Flachbart | F04B 43/12 417/53 |
| 2013/0165847 A1 | 6/2013 | Scarpaci et al. | |
| 2013/0291952 A1 | 11/2013 | Zhou | |
| 2014/0288488 A1* | 9/2014 | Distler | A61M 1/28 604/28 |

OTHER PUBLICATIONS

International Search Report for PCT/US2014/014467; dated May 19, 2014; 2 pages.

Supplementary European Search Report for EP14749592; date of completion Jan. 19, 2016; 2 pages.

\* cited by examiner

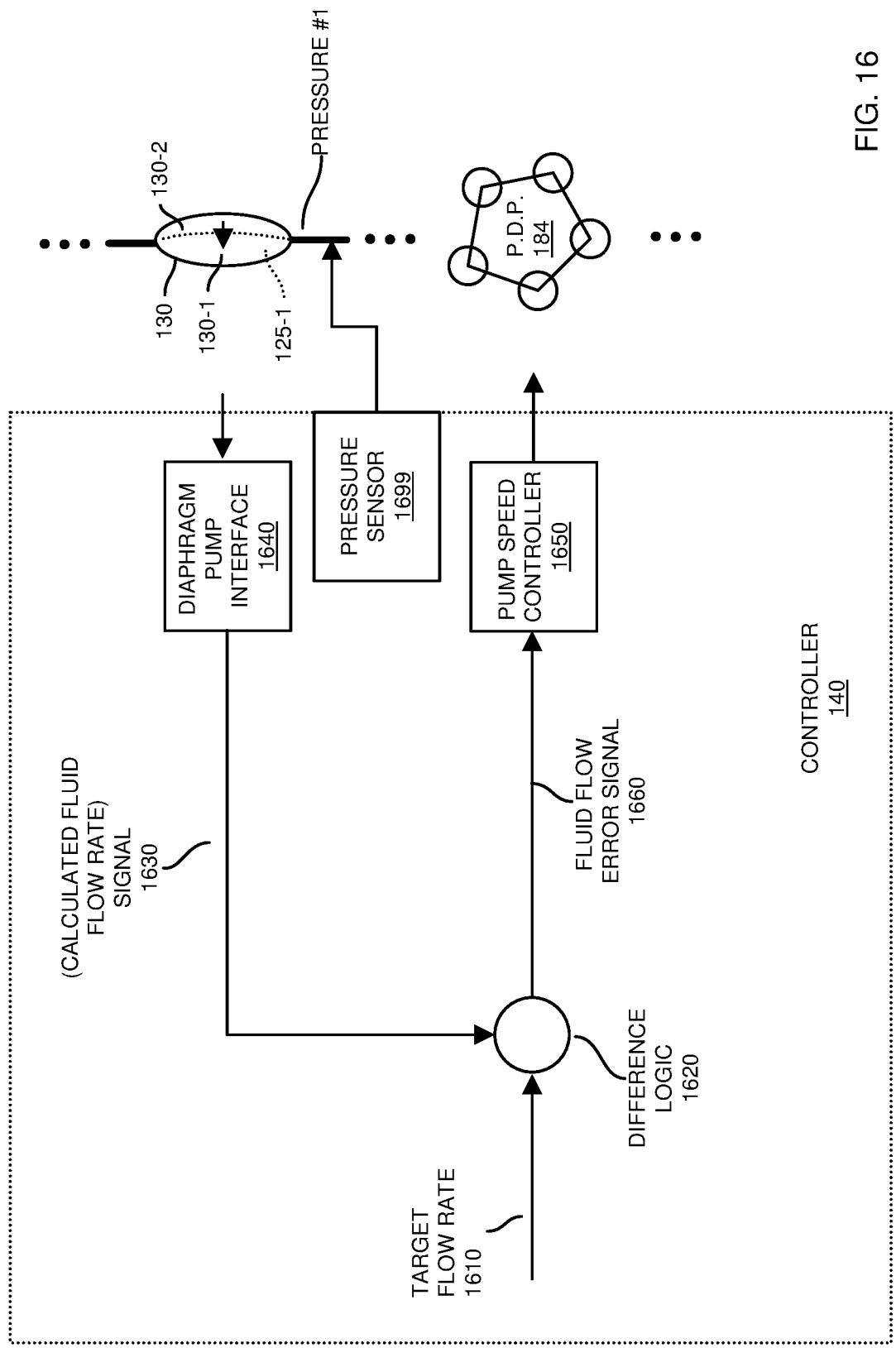

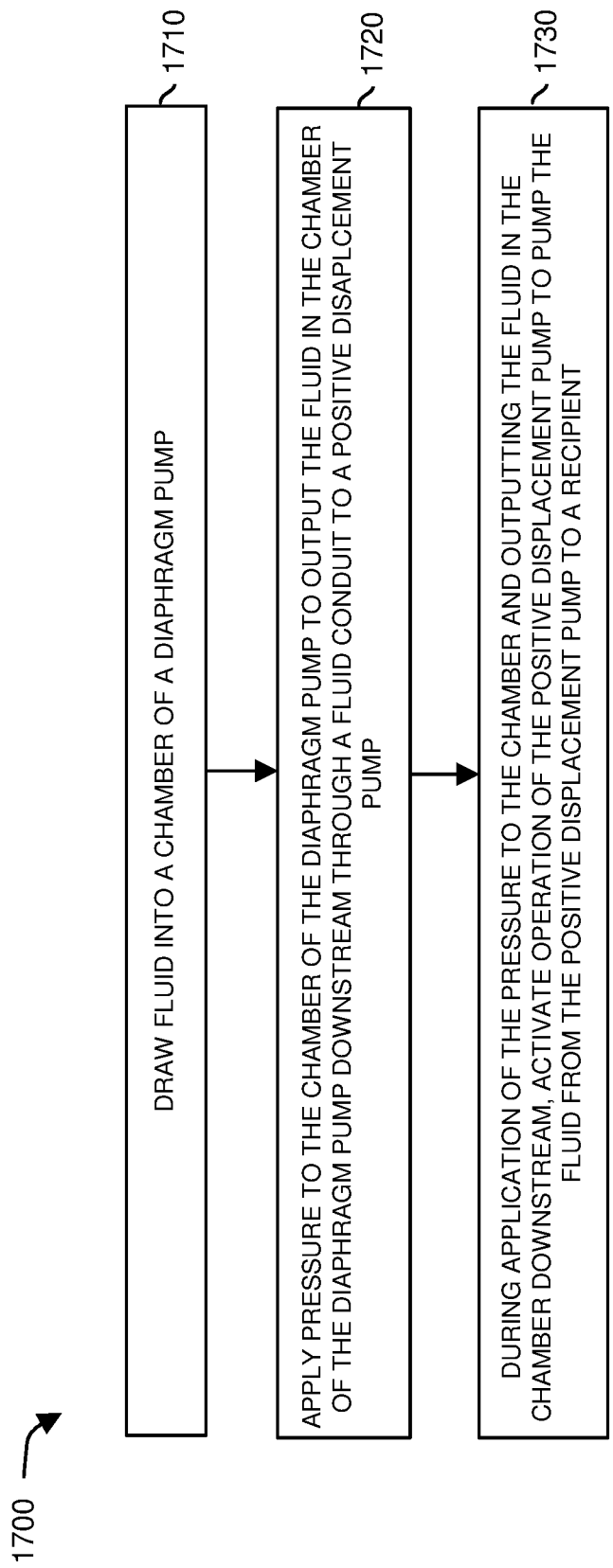

FLUID FLOW MEASUREMENT AND CONTROL

RELATED APPLICATIONS

This application is a continuation-in-part of U.S. patent application Ser. No. 15/468,546 entitled "FLUID FLOW MEASUREMENT AND CONTROL," filed on Mar. 24, 2017, the entire teachings of which are incorporated herein by this reference.

U.S. patent application Ser. No. 15/468,546 is a continuation-in-part of U.S. patent application Ser. No. 14/171,433 entitled "FLUID FLOW MEASUREMENT AND CONTROL," filed on Feb. 3, 2014, the entire teachings of which are incorporated herein by this reference.

U.S. patent application Ser. No. 14/171,433 claims the benefit of U.S. Provisional Patent Application Ser. No. 61/761,109 entitled "Measurement and Control of Fluid Flow in an Intravenous Pump," filed on Feb. 5, 2013, the entire teachings of which are incorporated herein by this reference.

BACKGROUND

Conventional techniques of delivering fluid to a recipient can include drawing a fluid from a fluid source into a chamber of a diaphragm pump. After the chamber is filled, a respective fluid delivery system applies a pressure to the chamber causing the fluid in the chamber to be delivered to a corresponding patient. The rate at which the fluid is delivered to the recipient may vary depending upon the magnitude of pressure applied to the chamber.

Eventually, after applying pressure to the chamber for a sufficient amount of time, all of the fluid in the chamber is delivered to the recipient.

In most applications, the amount of fluid drawn into the chamber of the diaphragm pump is substantially less than the amount of fluid to be delivered to the patient in total. To deliver the appropriate amount of fluid to the patient over time, the fluid delivery system repeats the cycle of drawing fluid from the fluid source into the chamber, and then applying pressure to the chamber to deliver the fluid to the recipient.

According to conventional techniques, based on the amount of elapsed time between time successive operations of drawing fluid into and expelling the fluid out of the chamber in the diaphragm pump, the fluid delivery system is able to determine the rate at which fluid is delivered to a corresponding patient.

BRIEF DESCRIPTION OF EMBODIMENTS

Embodiments herein are novel over conventional methods.

For example, in a general embodiment, to determine a fluid flow to a recipient, the fluid delivery system as described herein includes a valve disposed between a first volume (such as a chamber of known volume) and a second volume (such as a chamber of a diaphragm pump). The controller of the fluid delivery system initially closes the valve to prevent a transfer of gas between the first volume and the second volume. While the valve is closed, the controller controls a pressure of the second volume to deliver fluid in the diaphragm pump to a recipient. During a measurement of determining a capacity of the second volume and a rate of flow of fluid to the recipient, the controller opens the valve between the first volume and the second volume to enable a transfer of gas and to equalize the first volume and the second volume to substantially the same pressure. The controller calculates the magnitude of the second volume based at least in part on measured pressures of the gases before and after opening the valve.

As further discussed below, embodiments herein include improvements with respect to determining fluid flow rates. For example, as further discussed herein, embodiments herein include improvements such as temperature estimation, discontinuous pump operation, multiple pump embodiments, etc.

Temperature Estimation and Control

More specifically, in accordance with first embodiments, a fluid delivery system includes a first volume (such as a first chamber) and a second volume (such as a second chamber). Assume that the first volume is of a known magnitude and that the second volume is of an unknown magnitude. In one embodiment, a controller in the fluid delivery system controls magnitudes of pressures in the first volume and the second volume to deliver fluid to a corresponding recipient.

To produce a more accurate measurement of fluid delivered to a recipient, the controller estimates a temperature of gas in the first volume and a temperature of gas in the second volume. The controller estimates the temperatures based on measurements of pressure in the first volume and measurements of pressure in the second volume. In other words, in one embodiment, the controller derives the estimated gas temperatures at least in part from the measurement of pressures in the first volume and the second volume.

In addition to estimating temperatures, the controller as described herein can be configured to calculate a magnitude of the second volume based on a combination of measured pressures and estimated temperatures of the gases in the first volume and the second volume. Thermal effects of the first volume and/or the second volume can have an impact on calculated volume. In accordance with yet further embodiments, to estimate the temperature of gas in the first volume and the temperature of gas in the second volume, the controller derives the estimated temperature of the gas in the first volume and the estimated temperature of the gas in the second volume based at least in part on thermal effects due to changes in pressure of the gases in the first volume and the second volume.

Physical attributes of the first volume and the second volume can affect respective actual and estimated gas temperatures of the gases. In accordance with further embodiments, when estimating the temperature of gas in the first volume and the temperature of gas in the second volume, the controller can be configured to derive the temperature of the gas in the first volume and the temperature of the gas in the second volume based at least in part on an estimated transfer of heat between the gases and respective physical boundaries defining the first volume and the second volume.

By further way of non-limiting example, note that the second volume (as discussed above) can be a first chamber in a diaphragm pump. The diaphragm pump can include a second chamber disposed adjacent the first chamber. A flexible membrane in the diaphragm pump defines a boundary between the first chamber and second chamber. The controller controls a pressure applied to the first chamber (the second volume) to pump fluid in the second chamber to a target recipient. As described herein, the controller can apply negative pressure to the second volume to decrease a size of the second volume, drawing fluid into the second chamber of the diaphragm pump. The controller can apply positive pressure to the first chamber (second volume) to expel fluid from the second chamber of the diaphragm pump to a corresponding downstream recipient.

In accordance with still further embodiments, when the controller applies positive pressure to the second volume, the second volume changes over time as a result of delivering the fluid to the recipient. When estimating the temperature of gas in the first volume and the temperature of gas in the second volume, the controller can be configured to derive the temperature of the gas in the first volume and the temperature of the gas in the second volume based at least in part on a calculated change in the second volume over time.

In further embodiments, the controller uses the calculated magnitude of the second volume (volume of the first chamber in the diaphragm pump) to determine a flow rate of delivering fluid from the second chamber of the diaphragm pump to the target recipient.

Discontinuous Control Operation

In accordance with second embodiments, a controller in a fluid delivery system initiates drawing fluid into a chamber of a diaphragm pump. During a delivery phase, the controller applies positive pressure to the chamber. The applied positive pressure pumps the fluid in the chamber to a target recipient. At one or more times during the delivery phase, the controller temporarily discontinues or interrupts application of a pressure to the chamber to calculate how much of the fluid in the chamber has been pumped to the target recipient.

More specifically, assume that the fluid delivery system first initiates filling a chamber in a diaphragm pump. The fluid delivery system exerts pressure on the chamber to deliver a portion of the fluid in the diaphragm pump to a downstream recipient. The fluid delivery system temporarily discontinues application of pressure to the chamber. In one embodiment, discontinuing application of the pressure includes reducing a pressure applied to the chamber. The reduced pressure causes pumping of the fluid in the chamber to the recipient to slow down or stop for a short amount of time. The time of the interruption of pressure may be so short that it is unnoticeable or insignificant.

During such time of temporarily discontinuing application of a pressure, the fluid delivery system calculates the amount of the fluid remaining in the chamber of the diaphragm pump.

After calculating the amount of fluid remaining in the chamber, the fluid delivery system applies pressure to the chamber again, (potentially the same or substantially similar pressure applied prior to the interruption) causing the fluid in the chamber to resume normal delivery of fluid to the recipient. In other words, resumption of applying the pressure to the chamber causes the fluid in the chamber to flow again to the recipient.

In one embodiment, the fluid delivery system repeats this process of discontinuing application of the pressure to the chamber to calculate an amount of fluid remaining in the chamber multiple times during a delivery phase. Multiple measurements enable the fluid delivery system to accurately detect a rate of delivering fluid to a recipient over time.

In yet further embodiments, as mentioned, the controller can be configured to apply a substantially constant pressure (before and after a step of temporarily discontinuing application of pressure) to the chamber to evacuate the fluid from the chamber into a respective conduit that conveys the fluid to the target recipient.

Using the calculated amount of fluid remaining in the chamber at different times during the delivery phase, the controller can calculate a flow rate of delivering the fluid in the chamber to the target recipient.

In accordance with further embodiments, the controller can be configured to compare the calculated flow rate to a desired flow rate such as a set point. In response to detecting that a difference between the calculated flow rate and the desired flow rate is greater than a threshold value, the controller can be configured to adjust a flow rate of the fluid from the chamber to the target recipient to be nearer to the desired flow rate.

Note that the controller can modify any suitable control parameter to adjust a flow rate of the fluid if it is different than a respective desired set point. For example, in one embodiment, the controller adjusts a magnitude of the pressure applied to the chamber during the delivery phase to increase or decrease the fluid delivery rate. Additionally, or alternatively, the controller can be configured to adjust resistance of an in-line fluid flow resistor disposed between the chamber and the target recipient.

Discontinuing application of the drive pressure to the pump chamber can include controlling magnitudes of pressure in the pump chamber and a second reference to be dissimilar. The reference chamber can be a volume of known magnitude; the pump chamber can be a volume of unknown magnitude. In other words, as mentioned, the pump chamber can represent a varying volume, a magnitude of which varies as fluid is delivered to a recipient.

In further embodiments, the controller opens a valve between the reference chamber and the pump chamber to substantially equalize a pressure of gas in the reference chamber and the pump chamber. To more accurately calculate a rate of fluid delivery, as previously discussed, the controller can be configured to estimate the temperature of gas in the reference chamber and a temperature of gas in the pump chamber based on a measured pressure in the reference chamber and measured pressure of the pump chamber. The controller calculates how much fluid remains in the chamber based at least in part on measured pressures of the gases and the estimated temperatures of the gases in the reference chamber and the pump chamber.

Also, as previously mentioned, the controller can be configured to calculate how much of the fluid has been pumped to the target recipient based at least in part on how much of the fluid drawn into the pump chamber remains in the chamber after applying positive pressure to the pump chamber.

Multiple-Pump Embodiments

Further embodiments herein provide additional novel and improved fluid delivery over conventional techniques.

More specifically, in accordance with one or more additional embodiments, a fluid delivery apparatus includes controller hardware, a pneumatically (gas) driven diaphragm pump, a positive displacement fluid pump, and a fluid conduit (fluid tight pathway to convey fluid) extending between the diaphragm pump through the peristaltic fluid pump to a recipient. The diaphragm pump can be configured to receive the fluid from a remotely located fluid source. Accordingly, embodiments herein include a pressure controlled variable displacement pump (such as a diaphragm pump) feeding a force based variable positive displacement pump (such as a peristaltic fluid pump, rotary lobe pump, progressive cavity pump, rotary gear pump, piston pump, diaphragm pump, screw pump, gear pump, hydraulic pump, rotary vane pump, rope pump, flexible impeller pump, etc.). During operation of delivering fluid to a downstream recipient, the controller hardware initially draws fluid into a chamber of the diaphragm pump through the application of negative pressure. Subsequent to filling the chamber, the controller hardware applies positive pressure to the chamber of the diaphragm pump to output the fluid in the chamber (of the diaphragm pump) downstream through the fluid conduit to the positive displacement pump.

In one embodiment, the positive displacement pump includes an elastically deformable conduit (or segment) driven by a respective peristaltic fluid pump. During application of the pressure to the diaphragm chamber and outputting the fluid in the chamber downstream to the peristaltic fluid pump, the controller hardware activates the peristaltic fluid pump to pump force the fluid disposed in the segment from the peristaltic fluid pump along the fluid conduit to the downstream recipient. Accordingly, a diaphragm pump delivers fluid to the elastically deformable conduit; the peristaltic fluid pump then applies a peristaltic pump element in a sweeping motion to deliver the fluid in the segment downstream to a recipient.

More specifically, in one embodiment, the peristaltic pump element is in contact with and occludes (and/or pinches) the elastically deformable conduit. Via the occlusion or pinching, the peristaltic pump element blocks and controls a flow of the displacement of fluid from the diaphragm pump into the segment. Sweeping physical contact of the peristaltic pump element with respect to the elastically deformable conduit controllably conveys fluid in the elastically deformable conduit downstream to the recipient. Accordingly, in one embodiment, the peristaltic pump element performs multiple operations including: i) restricting (or holding back) a flow of the fluid received upstream of the peristaltic pump element from the diaphragm pump into the segment (elastically deformable conduit) as well as ii) controlling delivery of fluid in the segment (elastically deformable conduit) downstream of the peristaltic pump element to the recipient.

In accordance with further embodiments, a pressure of the fluid upstream of the peristaltic pump element is different than a pressure of the fluid downstream of the peristaltic pump element. More specifically, in one embodiment, a pressure of the fluid in a first portion of the fluid conduit upstream of the peristaltic pump element between the peristaltic pump element (that pinches, occludes, controls, etc., a flow of the fluid) and the diaphragm pump is greater than a pressure of the fluid in a second portion of the fluid conduit downstream of the peristaltic pump element.

In accordance with further embodiments, a pressure of the fluid in a first portion of the fluid conduit upstream of the peristaltic pump element between the peristaltic pump element (that pinches a flow of the fluid) and the diaphragm pump is less than a pressure of the fluid in a second portion of the fluid conduit downstream of the peristaltic pump element.

In accordance with another embodiment, the controller hardware of the fluid delivery apparatus as described herein is further operable to: measure a rate of fluid expelled from the chamber of the diaphragm pump downstream to the segment of fluid conduit. In one embodiment, the controller hardware uses a measured rate of expelled fluid from the chamber to control a rate of moving motion of the peristaltic pump element to regulate the delivery of the fluid to the recipient at a desired flow rate.

The flow rate of fluid through the diaphragm pump can be measured in any suitable manner. For example, in one embodiment, the controller hardware is further operable to: cyclically receive (draw), over each of multiple cycles, a quantum of the fluid from a disparately located fluid source container into the chamber of the diaphragm pump at each of multiple fill times.

In one embodiment, the controller hardware applies a negative pressure to the chamber of the diaphragm pump to draw the fluid from the fluid source container. If desired, the controller hardware can be configured to draw the fluid from the fluid source container into the chamber of the diaphragm pump during a condition in which a peristaltic pump element of the peristaltic fluid pump is in physical contact with the segment of fluid conduit and blocks the flow of the fluid received from the diaphragm pump through the segment. Thus, because the peristaltic pump element blocks fluid flow, instead of drawing fluid from the elastically deformable conduit into the chamber, the diaphragm pump draws the fluid from the upstream fluid source container.

In accordance with further embodiments, forces of gravity can be used as a way to fill the chamber of the diaphragm pump. For example, the container of fluid can be disposed above the diaphragm pump. Accordingly, negative pressure may not be needed to draw fluid into the chamber.

As previously discussed, subsequent to drawing the fluid into the chamber of the diaphragm pump, the controller hardware applies pressure to the chamber of the diaphragm pump to deliver the fluid in the chamber downstream to the peristaltic pump.

In yet further embodiments, to provide precise fluid flow control over a large possible range, the controller hardware measures a flow rate of fluid delivered to the recipient based upon measurements of remaining portions of fluid in the chamber over time. For example, in one embodiment, the controller hardware is operable to measure a flow rate of the fluid expelled from the chamber of the diaphragm pump downstream to the segment of the fluid conduit. As previously discussed, a peristaltic pump element of the peristaltic fluid pump controllably blocks a flow of the fluid received from the diaphragm pump to the recipient. The controller hardware utilizes the measured flow rate of the fluid (as detected from measuring respective remaining portions of fluid in the chamber of the diaphragm pump) to control (adjust) a sweep rate of moving the peristaltic pump element along the segment of the fluid conduit to provide delivery of fluid from the peristaltic pump element (and corresponding elastically deformable conduit) to the recipient as specified by a desired flow rate setting (such as a user selected rate).

If the measurement of fluid flowing through the diaphragm pump is greater than the desired flow rate setting, the controller hardware decreases the rate of sweeping the peristaltic pump element (which directly controls a rate of delivering fluid to a recipient). Conversely, if the measurement of the fluid flowing through the diaphragm pump as detected by the controller hardware is less than the desired flow rate setting, the controller hardware increases the rate of sweeping the peristaltic pump element. Accordingly, in one embodiment, the measured rate of fluid flow through the diaphragm pump can be used as a basis to control the downstream peristaltic pump to provide accurate fluid flow.

In accordance with yet further embodiments, the controller hardware, at each of multiple measurement times between a first time of filling of the chamber and a next successive time of filling the fluid into the chamber from a fluid source, temporarily changes a magnitude of the pressure at each of multiple sample windows to the chamber to measure a rate of delivering the fluid from the chamber downstream to the segment. More specifically, according to one embodiment, the controller hardware further controls the peristaltic pump element in contact with the segment of fluid conduit to continuously move along a length of the segment to provide corresponding continuous flow of fluid from the segment to the recipient in a time window. During each of multiple measurement windows, the controller hardware measures a respective portion of fluid remaining in the diaphragm pump to determine a respective fluid flow rate.

The controller hardware utilizes the respective measured portions of fluid remaining in the diaphragm pump as measured during the multiple measurement windows to calculate a rate of fluid delivered by the peristaltic fluid pump to the recipient. As previously discussed, in one embodiment, the peristaltic fluid pump can be configured to include a corresponding peristaltic pump element in physical contact with the segment of fluid conduit, the pump element controlling an amount of the fluid received at the elastically deformable conduit from the diaphragm pump.

Embodiments herein including a diaphragm pump (to measure a fluid delivery rate) and a peristaltic fluid pump (to control physical pumping transfer of fluid to a recipient) are advantageous over conventional techniques. For example, according to embodiments herein, inclusion of a diaphragm pump provides a way to measure a flow rate of fluid, provides a way (using negative pressure) to draw fluid from a source, and provides a constant and reliable pressure of fluid to the inlet of a peristaltic fluid pump.

The fluid delivery apparatus and corresponding methods as described herein provide one or more of the following advantages over conventional techniques: i) fast start and stop time to reach desired delivery flow rate set point, ii) large dynamic range to control flow rates from 0.1 or lower to 1200 or higher, iii) flow rate control that is immune to inlet or outlet pressure changes, iv) flow rate control that is immune to large variations in fluid properties (such as viscosity), real-time flow measurement for improved safety, and so on.

In accordance with yet further embodiments, a controller applies a drive pressure to fluid in a chamber of a diaphragm pump; the applied drive pressure causes flow of the fluid out of the chamber in a downstream direction from the diaphragm pump through a conduit. The controller temporarily discontinues application of the drive pressure to the chamber to calculate a portion of the fluid remaining in the chamber. After the temporary termination of pressure, the controller then resumes application of the drive pressure to the chamber. The resumed application of drive pressure causing resumed flow of the remaining fluid from the chamber through the conduit.

Further embodiments herein include, via a controller, controlling a valve disposed between the diaphragm pump and a second fluid pump. Control of the valve adjusts a flow rate of the fluid from the first fluid pump through the second fluid pump to a recipient. In one embodiment, the valve is repeatedly opened and closed at different times to the flow of fluid to from the first fluid pump to the second downstream fluid pump.

Yet further embodiments herein include, via a controller, controlling a flow of fluid from different fluid sources (such as any number of one or more sources, each of a same or different type of fluid) into the first fluid pump. Thus, the first fluid pump can be configured to receive different types of fluid such as a first type of fluid from a first source, a second type of fluid from a second source, and so on.

Still further embodiments herein include, via an air elimination filter (or other suitable resource) disposed in the conduit between the diaphragm pump and a second fluid pump, a means for removing gas from the flowing fluid.

In accordance with further embodiments, the controller controls a rate of fluid flowing through the first fluid pump via operation of a second fluid pump such as a positive displacement pump.

Further embodiments herein include, via the controller, and in addition to monitoring and controlling the first fluid pump, calculating a flow rate of delivering the fluid from the diaphragm pump downstream through the conduit based on calculated amounts of fluid in a chamber of the first fluid pump at multiple different times during a delivery phase.

As another example embodiment, via control of the second fluid pump such as a positive displacement pump, the controller blocks a flow of fluid from the first fluid pump to a recipient.

In yet further embodiments, via the second fluid pump coupled to receive the fluid from the diaphragm pump through the conduit, the controller controls a flow of the fluid through the conduit and the second fluid pump to a downstream recipient. In one embodiment, the controller controls the flow of fluid from the second fluid pump based on feedback indicating a rate at which the first fluid pump (diaphragm pump) delivers the fluid through the conduit.

Still further embodiments herein include utilizing a measured rate of fluid flow through the first fluid pump to control a rate of operating a second fluid pump. The controller controls delivery of fluid from the second fluid pump to a recipient at a flow rate as specified by a flow rate setting.

In yet further embodiments, the first fluid pump is a first diaphragm pump and the second fluid pump is a positive displacement pump, although each of the first fluid pump and the second fluid pump can be any suitable type of fluid pump.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: control magnitudes of pressure in a first volume and a second volume, the first volume being of a known magnitude, the second volume being of an unknown magnitude; estimate a temperature of gas in the first volume and a temperature of gas in the second volume based on measurements of pressure in the first volume and measurements of pressure in the second volume; and calculate a magnitude of the second volume based on measured pressures of the gases and estimated temperatures of gases in the first volume and the second volume.

Another embodiment herein includes a computer readable storage medium and/or system having instructions stored thereon. The instructions, when executed by computer processor hardware, cause the computer processor hardware to: initiate drawing fluid into a chamber of a diaphragm pump; during a delivery phase of pumping the fluid in the chamber to a target recipient, applying pressure to the chamber; and at multiple different times during the delivery phase, temporarily discontinuing application of the pressure to the chamber to calculate how much of the fluid in the chamber has been pumped to the target recipient.

Yet another embodiment herein includes a computer readable storage medium and/or system having instructions stored thereon. The instructions, when executed by computer processor hardware, cause the computer processor hardware to: control magnitudes of pressure in a first volume and a second volume to be dissimilar, the first volume being of a known magnitude, the second volume being of an unknown magnitude; initiate opening a valve between the first volume and the second volume to equalize a pressure in the first volume and the second volume; estimate a temperature of gas in the first volume and a temperature of gas in the second volume based on a measured pressure in the first volume and measured pressure of the second volume; and calculate a magnitude of the second volume based on measured pressures of the gases and estimated temperatures of the gases in the first volume and the second volume.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for use in delivering fluid to a recipient. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

FIG. 16 is an example diagram illustrating control of a respective positive displacement pump based upon a calculated fluid flow rate of fluid delivered by a respective diaphragm pump according to embodiments herein.

FIG. 17 is an example diagram illustrating a method of delivering fluid to a respective recipient using a combination of a diaphragm pump and a positive displacement pump according to embodiments herein.

Figure 1:
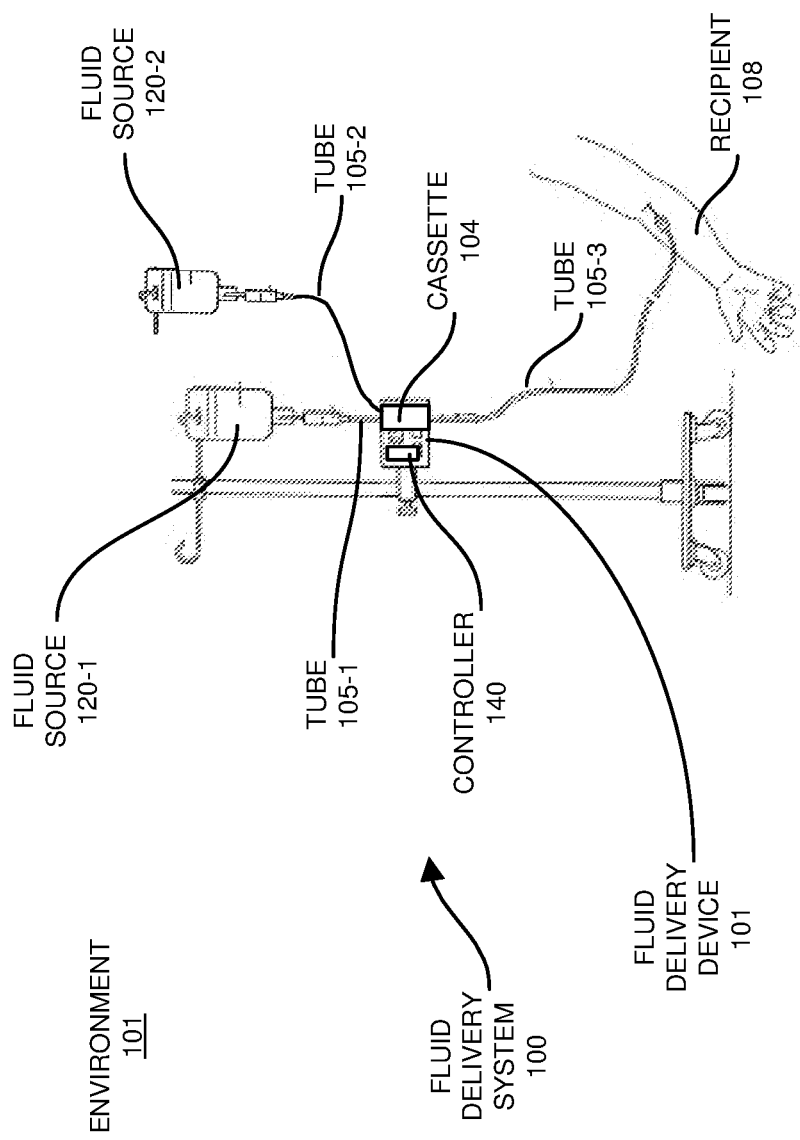
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

The fluid delivery system as described herein uses a system of valves, variable flow restrictions, reference volumes, direct pressure measurements, etc., to accurately deliver intravenous fluids to a recipient such as a patient. Typically fluids are introduced to the patient through a vein in the hand or arm. The pressure in the vein is typically on the order of 5 mm of Hg above atmosphere.

Conventional fluid pumps currently available in the market require that a respective fluid source be in a prescribed location with respect to the pump. Likewise, the pump must be in a prescribed location with respect to the patient. Variation in either source location or downstream pressure conditions can cause flow rate inaccuracy due to the affects of system pressures on the pumping mechanism. It is desirable for many reasons in a clinical setting for the pump to be able to deliver the fluid to the patient irrespective of the source or outlet pressure conditions. In certain instances when a peristaltic fluid pump is used, wear-out of respective elastic regions in the peristaltic pump can cause inaccuracy as well. More specifically, as respective tubing becomes worn and fatigued, it doesn't rebound fully. In such an instance, the "stroke" of each cycle (volume of fluid delivered in each stroke cycle) is diminished.

Embodiments herein use compressed gas (air) to induce the required differential pressures needed to move the fluid into the patient under a wide range of relative positions of the pump, the patient, and the fluid source. The fluid to be delivered may be below the patient or above the patient. The pump may be above or below the patient regardless of the fluid location. In certain instances, it is desirable that the fluid be delivered with as low a pressure as possible and at a continuous flow rate. The pump is able to use low pressure and accommodate a variety of relative pump and/or patient positions because the system can measure flow rate and adjust for any variations away from the target flow rate.

There are primarily two types of IV pumps on the market today; syringe and linear peristaltic pumps. Both are positive displacement pumps, which can present very high pressures to the patient in many circumstances. There are many limitations of this technology. As an example, in order to mitigate this risk, pressure sensors are added to detect dangerously high pressures and stop the pump. Due to the configuration of this technology and the elasticity of the tubing, large boluses of fluid are often injected to the patient inadvertently. In contrast, by using drive pressure directly to push the fluid to the patient rather than a rigid mechanical piston any disturbances stop the pump directly without the need for a detection system.

Now, more specifically, FIG. 1 is an example diagram illustrating a fluid delivery system according to embodiments herein.

As shown, fluid delivery environment 101 includes fluid delivery system 100. Fluid delivery system 100 includes fluid source 120-1, fluid source 120-2, and recipient 108. Fluid delivery system 100 includes controller 140 as well as cassette 104, facilitating delivery of fluid from one or more fluid sources 120 to the recipient 108.

In one embodiment, the cassette 104 is a disposable cartridge inserted into a cavity of a housing of the fluid delivery system 100. During delivery, fluid from the different fluid sources 120 is limited to contacting (disposable tube set including) cassette 104, tubes 103, and its corresponding components as further discussed below. When delivering fluid to a different patient, a caregiver inserts a new cassette into the cavity of fluid delivery system 100. The new cassette includes a corresponding set of new (sterile) tubes. Thus, the fluid delivery system 100 can be used for many patients without having to be cleaned.

As mentioned, during operation, the controller 140 of fluid delivery system 100 controls delivery of fluid from one or more fluid sources 120 (such as fluid source 120-1 and/or fluid source 120-2) to recipient 108. As shown in this example embodiment, tube 105-1 conveys fluid from fluid source 120-1 to cassette 104. Tube 105-2 conveys fluid from fluid source 120-2 to cassette 104. Note that fluid source 120-1 and fluid source 120-2 can store the same or different fluids.

The controller 140 controls one or more components in cassette 104 to deliver fluid received from fluid source 120-1 and/or fluid source 120-2 through tube 105-3 to recipient 108.

Control System:

By way of a non-limiting example, a mass flow based measurement system takes into account the ideal gas laws and mass conservation. The equations hold for a closed system.

$$M_{a1} + M_{b1} = M_{a2} + M_{b2} \qquad \text{(equation 1)}$$

$$PV = MRT \rightarrow M = \frac{PV}{RT} \qquad \text{(equation 2)}$$

R is a constant, so the equations factor down to:

$$\frac{P_{a1}}{T_{a1}} V_a + \frac{P_{b1}}{T_{b1}} V_b = \frac{P_{a2}}{T_{a2}} V_a + \frac{P_{b2}}{T_{b2}} V_b \qquad \text{(equation 3)}$$

Estimation of temperatures as disclosed herein enables quick measurements and allows the device to operate without stopping the flow during measurements by taking into account the full system states (such as temperature), rather than assuming that they remain constant through the cycle.

More specifically, in one embodiment, an appropriate drive pressure can be applied to a drive chamber side of a diaphragm pump to initiate delivery of fluid in a fluid chamber side of the diaphragm pump to a target recipient. Further embodiments herein can include discontinuing application of the pressure to the drive chamber at one or more times during a delivery cycle to perform a volume check to identify how much of the fluid is present in the fluid chamber of the diaphragm pump over time.

In one embodiment, the flow rate of fluid pumped to a target recipient equals the change in volume of the drive chamber over time.

During times of discontinuing application of the pressure to the diaphragm pump, embodiments herein can include taking into account changes in temperature of the gases (as a result of changing pressures) in one or more chambers when calculating the flow rate of delivering the fluid to the target recipient.

In one embodiment, a mass balance measurement is dependent on the temperature of the working fluid. Given required measurement speed noted above, the gas experiences adiabatic heating and cooling during the measurement cycle. It may be difficult if not impossible to measure (with a temperature sensor) the gas temperature directly in the time frame needed; therefore a thermal estimator is used to predict the gas temperature. In other words, the temperature of gases in one or more volumes as discussed herein can change so quickly that a physical temperature sensor is unable to detect a respective change in temperature.

Figure 4:
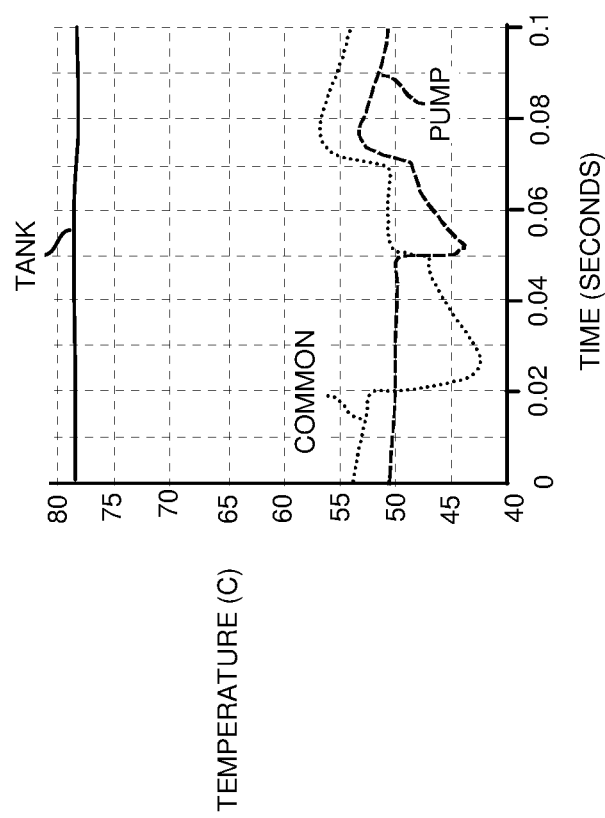
FIG. 4 is an example diagram illustrating a change in hypothetical gas temperatures during a fluid measurement cycle according to embodiments herein.

FIG. 4 is a hypothetical example diagram illustrating gas temperatures in different resources during a delivery cycle. As described herein, one or more temperatures can be estimated based on known system information as discussed in more detail below.

In one embodiment, there are several additions to the ideal gas law approach that are used to achieve the required performance characteristics for a safe and reliable infusion pump. First there are common conditions when the flow rate is low and the outlet pressure is low such as when the pump is significantly higher than the patient. In this case, the required drive or pumping pressure is also very low. Very low drive pressures are difficult to measure with common low cost pressure transducers and it is very difficult to accurately control and maintain low pressure in the positive tank. At higher flow rates or higher outlet pressure, the drive pressures needed are much higher. This wide dynamic range makes it difficult to maintain pressure measurement resolution.

In order to: i) achieve all of the desired flow rate range given the relatively wide range of outlet pressure, ii) maximize pressure measurement resolution, and iii) maintain a driving pressure high enough to avoid low pressure measurements near atmosphere, embodiments herein can include a variable flow restriction that is added downstream of the pump chamber.

By way of a non-limiting example, this flow restriction can be a variable orifice. Given a desired set point flow rate, the variable fluid restriction opening is changed to maintain a minimum drive pressure. This variable fluid restriction further serves as a safety mechanism that can be positively shut or closed if desired. Another requirement of infusion systems may be to maintain continuous flow. In one embodiment, the fluid delivery system as discussed herein does not stop the pumping during a flow rate measurement. Thus, embodiments herein can include providing a continuous or substantially continuous flow of fluid delivery to a respective target recipient.

In order not to introduce measurement error, the volume measurement cycle can be performed extremely fast such as on the order of milliseconds. According to embodiments herein, a measurement cycle can be less than 200 milliseconds. The fill cycle, such as filling the chamber of the diaphragm pump with fluid, also can be performed very fast to minimize flow variation.

When the gases are moved at this high speed for all of the reasons above the isothermal Ideal Gas Law and Boyle's Law begin to breakdown. Specifically the assumption that the gas is isothermal is no longer true. It is observed that the gas experiences adiabatic heating and cooling during the measurement cycle. As previously discussed, embodiments herein include estimating gas temperatures to compensate for these errors.

In order to account for the temperature effects due to adiabatic heating and cooling of the gas the pressure and volume relationships are transformed as described above to yield:

$$V_{pc} = V_{com} \frac{\left(\frac{P_{com2}}{T_{com2}} - \frac{P_{com1}}{T_{com1}}\right)}{\left(\frac{P_{pc1}}{T_{pc1}} - \frac{P_{pc2}}{T_{pc2}}\right)} \quad \text{(equation 4)}$$

By way of a non-limiting example, the temperature can be estimated by tracking the system state variables at each time step of the control loop. The physical parameters of the delivery system, such as volume, orifice size, and heat transfer coefficients combined with the measured pressures allow the system to calculate an estimated temperature in each of the gas volumes at any point during the pumping cycle using the following energy balance equation:

$$\frac{dT_i}{dt} = \frac{1}{M_i C_v}\left[C_p \sum_j T_j Q_{ji} - C_p T_i Q_{out} - C_v T_i(Q_{in} - Q_{out}) + H(T_{wall} - T_i)\right] - \left(\frac{C_p}{C_v} - 1\right) \cdot \frac{T_i}{V_i} \frac{dV_i}{dt} \quad \text{(equation 5)}$$

Where:
V=volume
Cv=specific heat at constant volume
Cp=specific heat at constant pressure
T=temperature
Q=mass flow
H=heat transfer coefficient More Detailed Description of Embodiments In one non-limiting example embodiment, the fluid pumping system as described herein is centered around a pumping chamber ("IPC"—Intermediate Pumping Chamber) that consists of a volume bifurcated by a flexible diaphragm. One side of the IPC is connected to the pneumatic portion of the fluidic system. The other side of the IPC is connected to the hydraulic portion of the fluidic system. Hydraulic pumping is achieved by applying alternating positive and negative pressure to the pneumatic side of the IPC, thus moving the diaphragm back and forth (or in and out).

Figure 2:
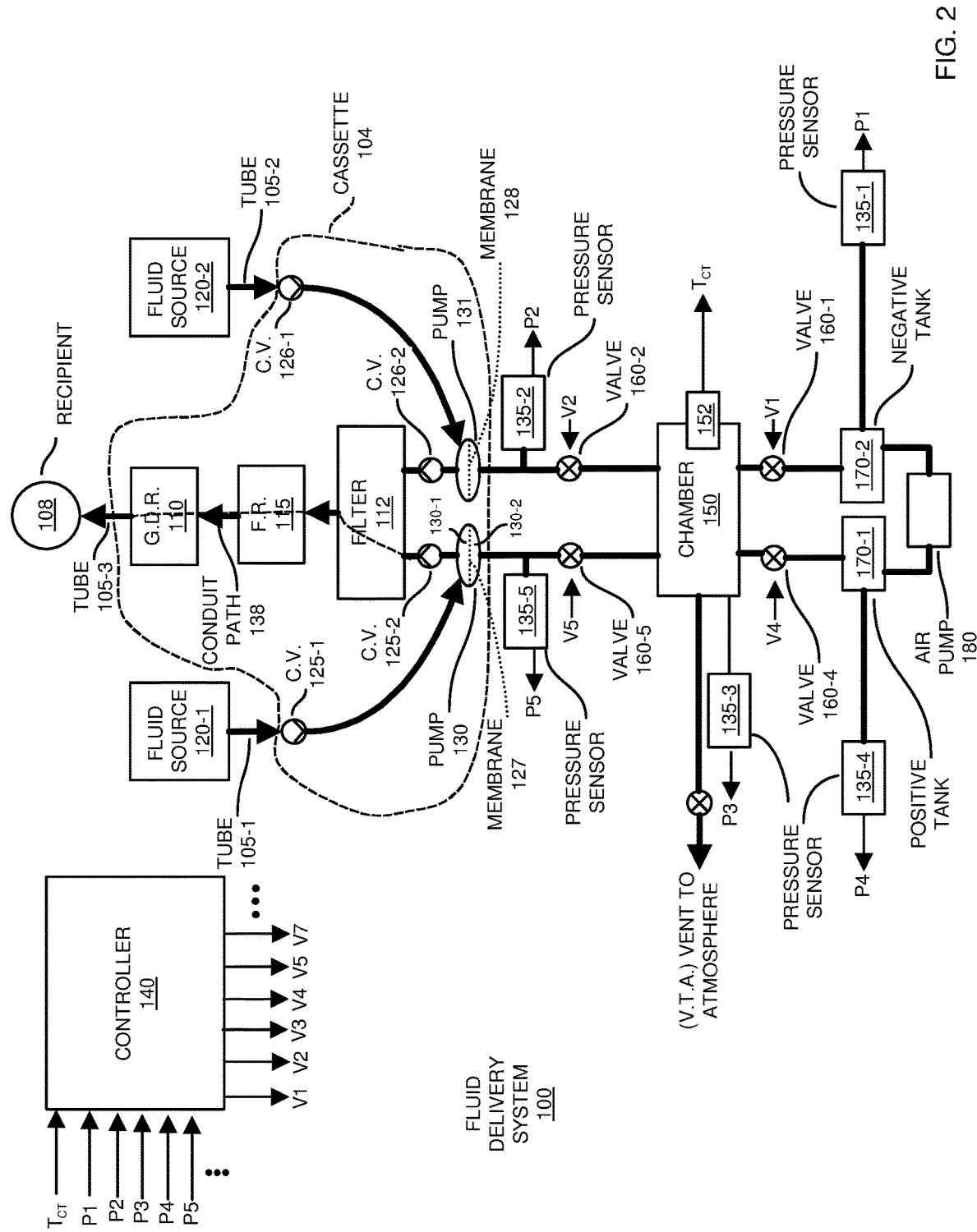
FIG. 2 is an example diagram illustrating more specific details of components and partitioning in a fluid delivery system according to embodiments herein.

FIG. 2 is a more specific example diagram illustrating components disposed in a fluid delivery system and corresponding disposable cassette according to embodiments herein.

As previously discussed, the controller 140 of the fluid delivery system 100 controls operation of diaphragm pumps 130 and 131 in disposable cassette 104 to precisely deliver fluid from one or more fluid sources such as fluid source 120-1 and fluid source 120-2 to a respective recipient 108.

In one embodiment, the flow of fluid through the system is controlled by adjustments to the drive pressure from the Positive Tank 170-1 and a variable hydraulic resistor (component such as fluid resistor 115) that is controlled by a motor or other suitable resource. Flow rate is measured using periodic volume calculations described below, and the control parameters are adjusted accordingly to drive the error between measured flow rate and target flow rate to zero.

Pump Cycle Overview

In accordance with yet further embodiments, a pump cycle is defined as a motion of drawing fluid into a diaphragm pump and then applying pressure to the diaphragm pump to deliver the fluid to a recipient. In accordance with a specific non-limiting example embodiment, a pump cycle can be defined as at least partially moving of the membrane 127 in the diaphragm pump 130 from one extreme (such as "full") to another extreme (such as "empty").

Figure 3:
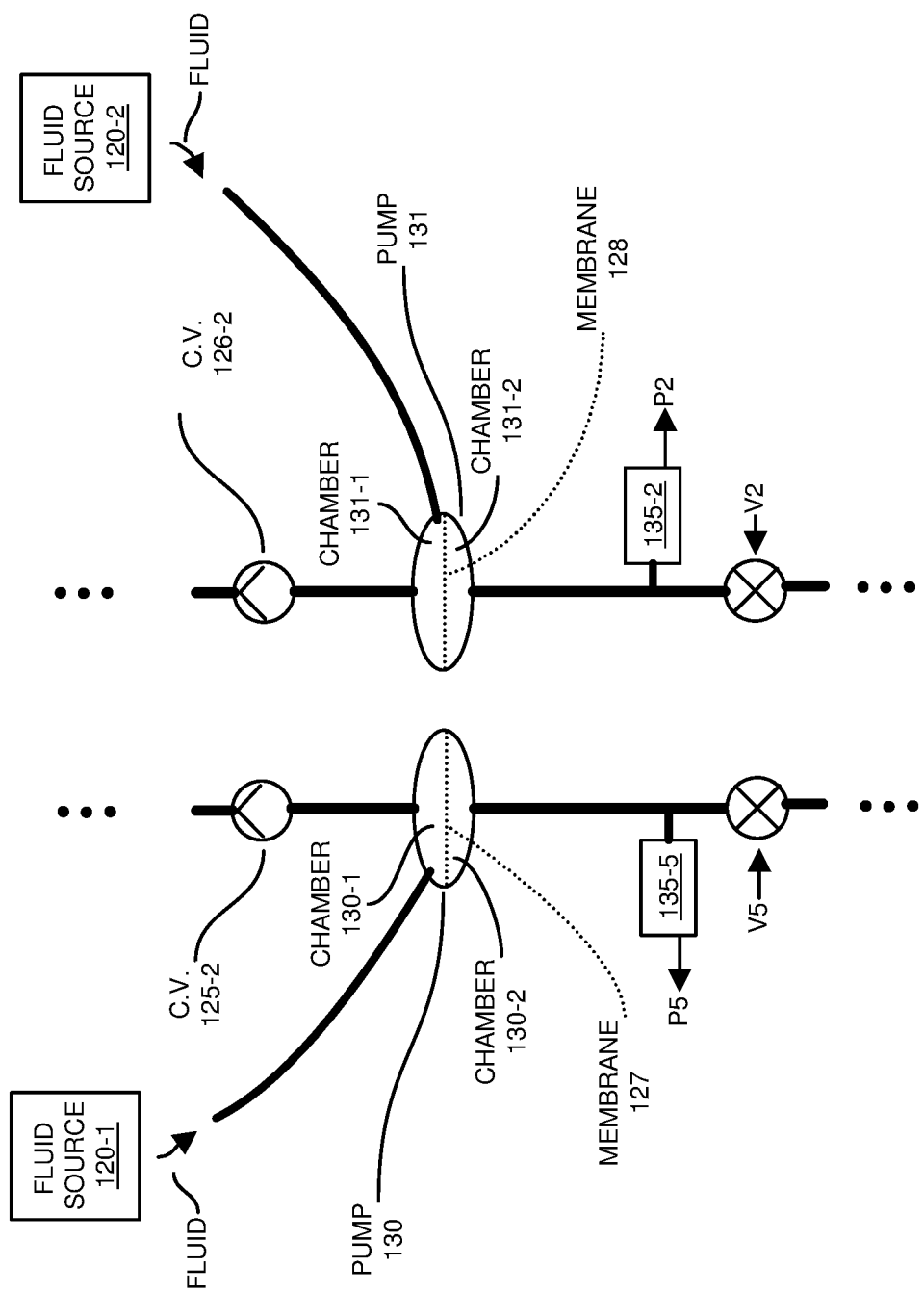
FIG. 3 is an example diagram illustrating details of a diaphragm pump used in a fluid delivery system according to embodiments herein.

As shown in FIG. 2 and more specific FIG. 3, membrane 127 divides the diaphragm pump 130 to include chamber 130-1 and chamber 130-2. Membrane 127 prevents fluid in chamber 130-1 from passing to chamber 130-2, and vice versa.

The membrane 127 dividing diaphragm pump 130 into chamber 130-1 and chamber 130-2 is flexible. When a negative pressure is applied to chamber 130-2, the volume of chamber 130-1 expands and draws fluid from fluid source 120-1 into chamber 130-1.

Conversely, when a positive pressure is applied to chamber 130-2, the volume of chamber 130-1 decreases expelling fluid from chamber 130-1 downstream to a respective recipient 108.

The total volume or capacity of chamber 130-1 and chamber 130-2 is substantially constant regardless of the position of the membrane 127. Based on knowing the volume of fluid in chamber 130-2, one is able to determine a corresponding volume of chamber 130-1. For example, if the total volume of the diaphragm pump 130 is Vtotal, and the volume of chamber 130-2 is V2, the fluid delivery system 100 can determine the volume of chamber 130-1 by subtracting V2 from Vtotal.

Diaphragm pump 131 operates in a similar manner as diaphragm pump 130.

Membrane 128 divides the diaphragm pump 131 to include chamber 131-1 and chamber 131-2. Membrane 128 prevents fluid in chamber 131-1 from passing to chamber 131-2, and vice versa.

The membrane 128 dividing diaphragm pump 131 into chamber 131-1 and chamber 131-2 is flexible. When a negative pressure is applied to chamber 131-2, the chamber 131-1 draws fluid from fluid source 120-2 into chamber 131-1. Conversely, when a positive pressure is applied to chamber 131-2, the diaphragm pump 131 expels fluid from chamber 131-1 downstream to a respective recipient 108.

In a similar manner as previously discussed for diaphragm pump 130, the total volume or capacity of chamber 131-1 and chamber 131-2 is substantially constant regardless of the position of the membrane 128. Based on knowing the volume of fluid in chamber 131-2, the controller 140 is able to determine a corresponding volume of chamber 131-1. For example, if the total volume of the diaphragm pump 131 is Vtotal, and the volume of chamber 131-2 is determined as being V2, the fluid delivery system 100 can determine the volume of chamber 131-1 by subtracting V2 from Vtotal.

In this example embodiment, as shown in FIG. 2, temperature sensor 152 measures a temperature (e.g., TTC) of gas in chamber 150 (common tank) and provides a baseline from which to estimate the temperatures of gases in one or more of the following resources: chamber 150, pump chamber 130-2, positive tank 170-1, negative tank 170-2, etc.

As further discussed below, estimation of the temperature enables a more accurate assessment of how much of fluid in pump chamber 130-1 has been pumped in a direction towards the target recipient 108 over conduit path 138 (such as a path from diaphragm pump 130 through a combination of check valve 125-2, filter 112, fluid resistor, gas detection resource 110, and tube 105-3 to recipient 108).

Initially, to fill the chamber 130-1 with fluid from fluid source 120-1, the controller 140 of fluid delivery system 100 applies a negative pressure or vacuum to chamber 130-2. At such time, pump chamber 130-2 reduces in volume, causing the chamber 130-1 to fill with fluid received from fluid source 120-1 through check valve 125-1. Check valve 125-1 prevents fluid from flowing in a backward direction from diaphragm pump 130 to fluid source 120-1. Check valve 125-2 prevents fluid from flowing in a backward direction from conduit path 138 to the pump chamber 130-1.

Assume that prior to filling, the chamber 130-1 is substantially empty of fluid. In one embodiment, to draw fluid into chamber 130-1 with negative pressure from tank 170-2 as discussed above, the controller 140-1 generates respective control signals V1 and V5 to open valve 160-1 and 160-5 (while all other valves are closed) to draw fluid from fluid source 120-1 and check valve 125-1 into chamber 130-1.

Subsequent to chamber 130-1 being filled with fluid, the controller 140 controls settings of the valves 160 to apply a positive pressure from tank 170-1 to chamber 130-2 of diaphragm pump 130. For example, via generation of control signals V4 and V5, the controller 140 opens valves 160-4 and 160-5 and closes all other valves. The flow of gas from positive tank 170-1 to pump chamber 130-2 causes pumping of fluid from chamber 130-1 through check valve 125-2 along conduit path 138 to the target recipient 108. As previously discussed, during application of positive pressure to chamber 130-2, check valve 125-1 prevents fluid in chamber 130-1 from flowing back into fluid source 120-1.

As shown, the conduit path 138 through cassette 104 can include filter resource 112 that eliminates air and/or particulate matter in the fluid from being pumped to the target recipient 108.

Additionally conduit path 138 can include an in-line flow resistor 115. In one embodiment, the controller 140 utilizes the in-line flow resistor as one means to control a rate of delivering fluid to the target recipient 108. For example, at a given driving pressure in chamber 130-2, to decrease a rate of flow, the controller 140 increases a resistance of the in-line flow resistor 115. To increase a flow rate of fluid from the chamber 130-1 to the target recipient 108, the controller 140 decreases a resistance of the in-line flow resistor 115.

Note that drive pressure in chamber 130-2 is another way to control a rate of delivering fluid to the target recipient 108. At a given position of an in-line flow resistor 115, the controller can use air pump 180 and pressure gauge 135-4 to set a target drive pressure in positive tank 170-1. That drive pressure can then be applied to pump chamber 130-2 (by opening valve 160-5) to drive the fluid in chamber 130-1 to target recipient 108. To increase a flow rate of fluid from the chamber 130-1 to the target recipient 108, the controller 140 can be configured to increase the drive pressure in positive tank 170-1. To decrease a flow rate the controller 140 can be configured to decrease the drive pressure in positive tank 170-1.

Note that conduit path 138 also can include gas detector resource 110. The gas detector resource 110 can be configured to detect presence of air (or other gases) in the fluid being pumped through conduit path 138 to the target recipient 108. Based on feedback from the gas detector resource 110 as monitored by the controller 140, the controller 140 can be configured to sound an alarm in the event of detecting presence of gas in the fluid pumped to the target recipient 108.

During a delivery phase, the controller 140 can be configured to mainly apply pressure to chamber 130-2 with gas from tank 170-1 or tank 150 to cause the fluid in chamber 130-1 to be pumped to the target recipient 108. Delivery of the fluid in chamber 130-1 through conduit path 138 to target recipient 108 can be controlled by the controller 140 in accordance with a pre-selected fluid delivery rate. In other words, the controller 140 controls positive pressure applied chamber 130-1 to control a respective fluid flow rate. As further discussed below, embodiments herein can include at least temporarily discontinuing application of pressure to chamber 130-2 in order to perform a measurement of fluid remaining in chamber 130-1. As shown and discussed, discontinuing application of pressure to chamber 130-2 can at least temporarily reducing a pressure in chamber 130-2.

During a fluid delivery phase, the controller 140 supplies a substantially constant pressure to the chamber 130-2. Because the membrane 127 is flexible, the pressure in chamber 130-2 exerts a force on the fluid in chamber 130-1. In general, via application of the appropriate pressure to chamber 130-2, the controller 140 is able to fairly accurately pump the fluid at a desired flow rate. However, in certain situations, the delivery system 100 can be perturbed, resulting in errors in the flow rate. For example, as previously mentioned, the fluid source 120-1 may be squeezed, the elevation of fluid source 120-1 may change, etc. Any of these conditions can impact an accuracy of a desired fluid delivery rate.

Note that in addition to applying positive pressure to the pump chamber 130-2 during a fluid delivery phase, embodiments herein can include occasionally checking how much of the fluid drawn into the chamber 130-1 has been pumped towards the target recipient 108 through conduit path 138. This enables the controller 140 to accurately determine the actual flow rate of fluid, even during times when the system conditions are perturbed.

More specifically, one way to measure a fluid delivery rate during a respective delivery phase is to repeatedly measure how much of the fluid in the chamber 130-1 has been pumped towards target recipient 108 on conduit path 138 at one or more MEASUREMENT times during the delivery phase. For example, the controller 140 the controller can initiate checking the volume of gas in chamber 130-2 over multiple sample times of a positive pressure delivery cycle. Because it is known how much gas is initially in the chamber 130-2 at the beginning of a delivery phase, and based on calculating how much gas is in chamber 130-2 at different times, etc., the controller is able to accurately measure a rate of pumping or delivering the fluid from fluid source 120-1 over conduit path 138 to the target recipient 108 in between times of filling the chamber 130-2. Thus, the controller 140 is able to accurately measure fluid delivery in very small increments of time between successive cycles of refilling the chamber 130-1 with additional fluid.

In one embodiment, as previously discussed, the total volume of the diaphragm pump 120-1 including chamber 130-1, chamber 130-2 and conduit there between is a known quantity. One embodiment herein includes calculating how much fluid remains in chamber 130-1 based on knowing the volume of chamber 130-2. That is, the volume of the chamber 130-1 can be calculated by subtracting the volume of chamber 130-1 from the total volume of diaphragm pump 130. As discussed below, the volume of chamber 130-2 is initially an unknown quantity but is calculated based on pressure and estimated temperature.

Figure 5A:
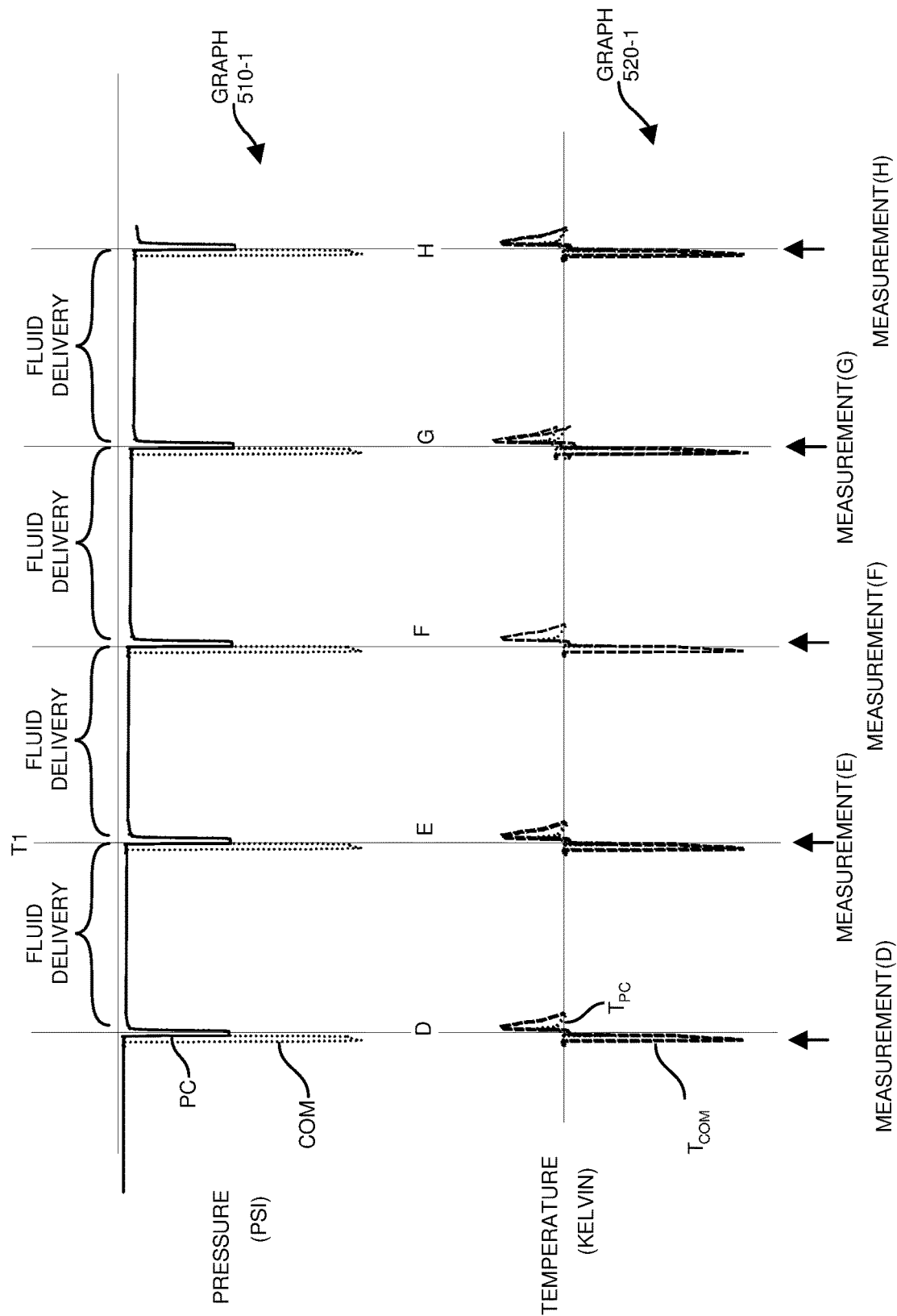
FIG. 5A is an example timing diagram illustrating application of different pressure to a diaphragm pump over time to deliver fluid to a target recipient according to embodiments herein.

FIG. 5A is an example diagram illustrating fluid measurements during fluid delivery according to embodiments herein. As shown, graph 510-1 illustrates application of pressure for more than 95% of a delivery cycle. PC represents the pressure of gas in chamber 130-2; COM represents the pressure of gas in the chamber 150.

In between times of applying pressure to chamber 130-2 (such as times labeled as FLUID DELIVERY), the controller 140 of fluid delivery system 100 periodically or occasionally, at multiple times, performs a measurement (labeled as MEASUREMENT) to determine a volume of chamber 130-2 of diaphragm pump 130. By way of non-limiting example embodiment, the controller 140 initiates applying an approximately constant pressure during FLUID DELIVERY portions of a fluid delivery cycle while the applied pressure to chamber 130-2 is reduced briefly during each respective MEASUREMENT.

In this example embodiment, graph 520-1 illustrates changes in temperature of respective gases that occur during each of the measurements. For example, Tcom represents the estimated temperature of the gas in the chamber 150; Tpc represents the temperature of gas in the chamber 130-2.

In general, in one non-limiting example embodiment, the duty cycle of performing measurements versus delivering fluid is relatively small. That is, in one non-limiting example embodiment, most of a fluid delivery cycle (delivery phase) can be used to deliver corresponding fluid in chamber 130-1 of pump 130 to recipient 108. For a small portion of the delivery cycle, the controller 140 operates respective resources to perform a corresponding volume MEASUREMENT of the chamber 130-2 as shown. Recall that after a volume of the chamber 130-2 is known, the volume of chamber 130-1 can easily be determined.

Figure 5B:
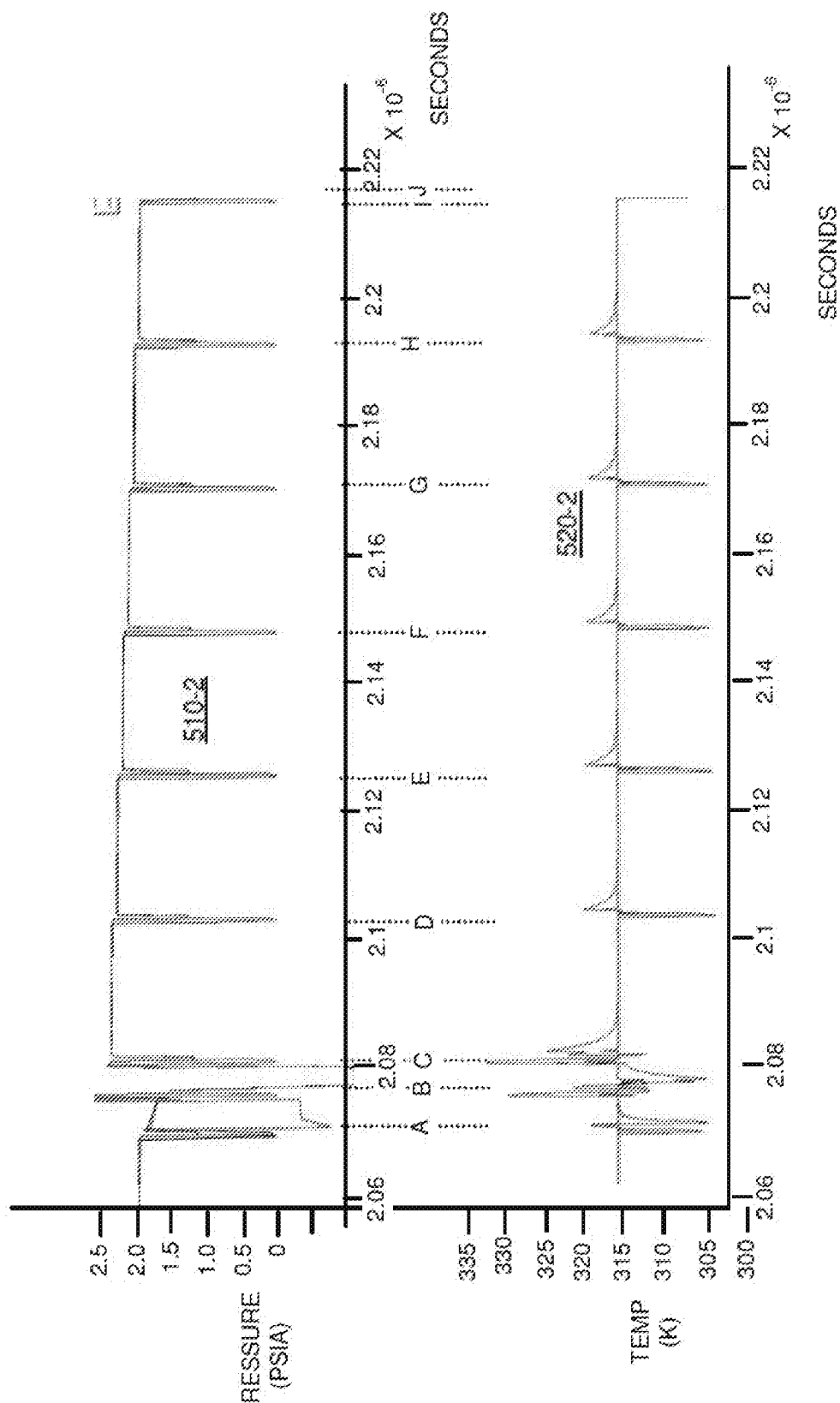
FIG. 5B is an example timing diagram illustrating application of different pressure to a diaphragm pump over time to deliver fluid to a target recipient according to embodiments herein.

FIG. 5B is an example diagram illustrating more particular details of a fluid delivery cycle according to embodiments herein.

Graph 510-2 shows the pressures measured in the system during a fluid delivery cycle. Graph 520-2 shows the estimated temperatures measured in the system during a fluid delivery cycle.

For the discussion here, the focus will be on pumping from the left hydraulic channel (e.g., from fluid source 120-1, through check valve 125-1, to diaphragm pump 130, through conduit path 138 to the target recipient 108), but the same patterns, behaviors and measurements apply to the right channel (e.g., from fluid source 120-2, through check valve 125-2, to diaphragm pump 131, to the target recipient 108) as well. As previously discussed, one or more diaphragm pumps can be operated in any suitable manner to deliver one or more fluids to a target recipient 108. For example, the controller 140 can individually and accurately control the flow rate of each of the fluids delivered to the target recipient 108.

In one non-limiting example embodiment, the controller 140 can pump a first fluid from fluid source 120-1 to the target recipient 108 at a first fluid delivery rate; the controller 140 can pump a second fluid from fluid source 120-2 to the target recipient 108 at a second fluid delivery rate, the first delivery rate can be different than the second delivery rate.

At or around time [A] in FIG. 5B, a delivery cycle begins by resetting the pressures in the positive tank 170-1 and negative tank 170-2. The controller 140 sets the solenoid valves 160-1, 160-2, 160-3, 160-4, and 160-5 (via generation of control signals V1, V2, V3, V4, and V5) to a closed position. The controller 140 activates (turns ON) air pump 180 to bring the tanks to the desired drive pressure.

At time [B], valves 160-1 (V1) and 160-5 (V5) are opened to apply the pressure in the negative tank 170-2 to the chamber 130-2. The negative pressure draws the diaphragm membrane 127 back towards tank 150, filling chamber 130-1 with fluid from fluid source 120-1. Check valve 125-1 (CV1) opens due to the differential pressure. Fluid such as liquid from fluid source 120-1 is drawn into the chamber 130-1 of the diaphragm pump 130.

At time [C] valves 160-4 (via generation of signal V4) and 160-5 (via generation of signal V5) are opened to apply the pressure in the positive tank 170-1 to the chamber 130-2 of the diaphragm pump 130. The positive pressure causes check valve 125-1 (CV1) to close and check valve 125-2 (CV2) to open. This causes the liquid in the chamber 130-2 of the diaphragm pump 130 to flow on conduit path 138 towards the target recipient 108 such as a patient.

In one embodiment, some time after the chamber 130-2 of diaphragm pump 130 is brought to positive pressure, the controller 140 performs volume calculations such as at times [D], [E], [F], etc. Aspects of the volume calculation are discussed in more detail below. As previously discussed, one or more volume calculations can be performed periodically during the time that the chamber 130-1 is emptying (e.g., during times [C] through [I]).

After the last volume measurement at time [I], or at any time during the delivery phase, the controller 140 calculates a flow rate from the volume measurements. Based on the calculated flow rate the controller 140 can determine if adjustments are needed to one or both of the two flow control parameters: target drive pressure in positive tank 170-1, in-line fluid resistance 115.

In general, increasing the pressure of gas in the chamber 130-2 of the diaphragm pump 130 increases the rate of fluid delivery; decreasing a magnitude of gas pressure applied to chamber 130-2 decreases a respective rate of fluid delivery.

Additionally, increasing an amount of fluid resistance provided by fluid resistor 115 reduces a rate at which the fluid in chamber 130-1 is delivered to the recipient 108; decreasing amount of fluid resistance provided by fluid resistor 115 increases a rate at which the fluid chamber 130-1 is delivered to the recipient 108.

The fluid delivery cycle restarts when the air pump 180 is turned on at time [J] to reset the pressures in the positive tank 170-1 and negative tank 170-2 again.

Measure Cycle Overview

Figure 6:
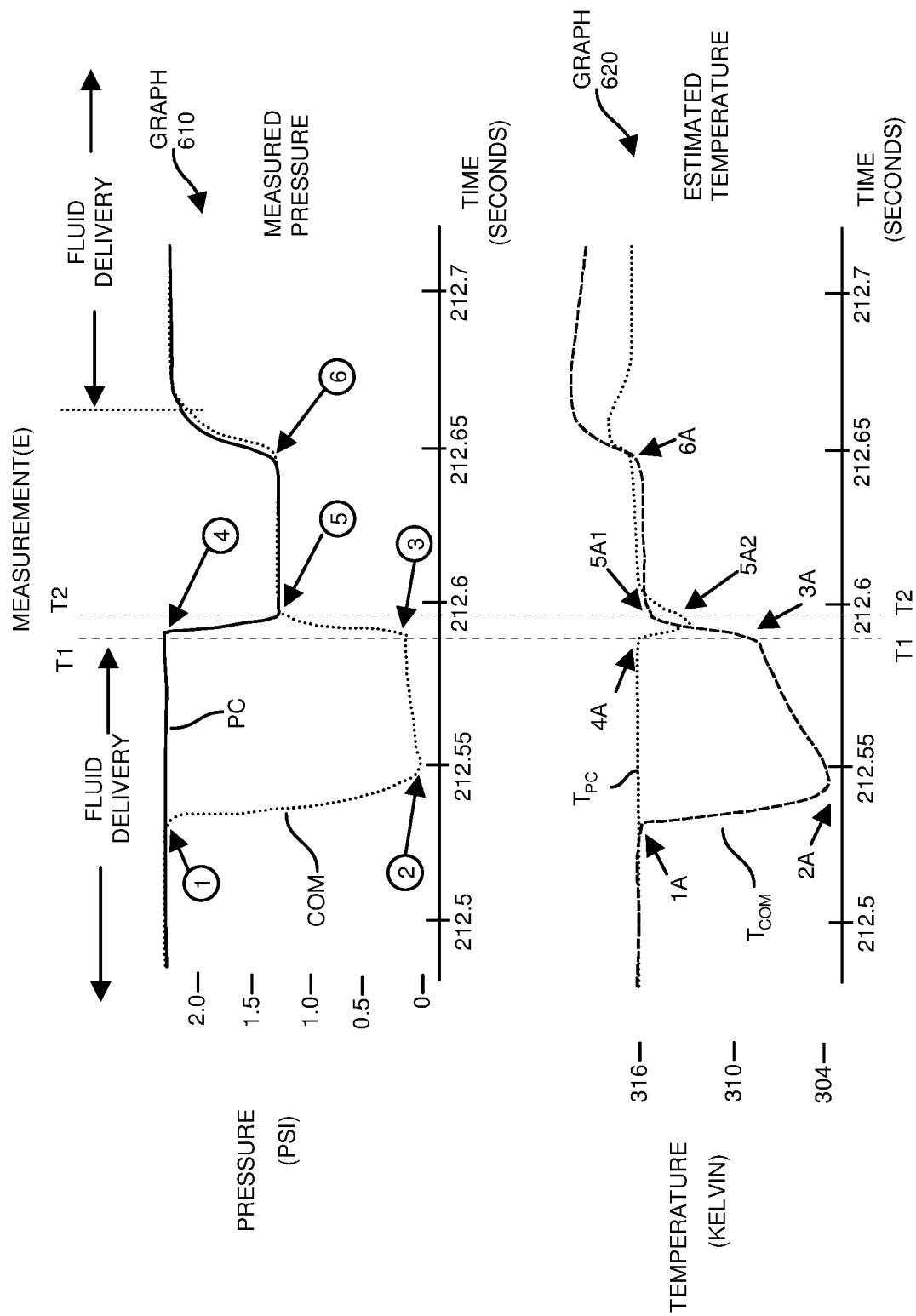
FIG. 6 is an example timing diagram illustrating temporary termination or reduction of applying positive pressure to a diaphragm pump and estimation of gas temperatures according to embodiments herein.

FIG. 6 is an example diagram illustrating a MEASUREMENT (time E) during a fluid delivery cycle according to embodiments herein.

Graph 610 illustrates gas pressures in each of multiple volumes. In this example embodiment, the pressure signal labeled PC in graph 610 represents the pressure of a gas in chamber 130-2 as measured by pressure sensor 135-5 (which produces pressure signal P5). The pressure signal labeled COM in graph 610 represents the pressure of a gas in chamber 150 as measured by pressure sensor 135-3 (which produces pressure signal P3).

Graph 620 illustrates estimated temperatures of the respective gases in the chamber 150 and chamber 130-2.

At the start of a respective fluid delivery cycle, the chamber 150 (Common Tank), positive tank 170-1, and the diaphragm pump 130 (e.g., Left IPC) are all at to the same pressure such as the driving pressure of the system. The driving pressure represents the pressure of the gas applied to chamber 130-2 prior to time T1.

At point [1] in graph 610, the controller 140 generates control signals V1, V2, V3, etc., to close all of the valves 160 to isolate the gas volumes. The controller controls valve 160-3 (via signal V3) to an open state to vent the chamber 150 (Common Tank) to ambient pressure.

When the pressure in the chamber 150 reaches ambient pressure at approximately point [2], the controller 140 controls valve 160-3 (via generation of signal V3) to a closed position again such that all of the gas volumes are again isolated.

After a brief stabilization period (such as approx. 50 milliseconds), at approximately time, T1, (shown as points [3] and [4]), the controller 140 controls valve 160-5 (via generation of signal V5) to an open state to merge the gas in chamber 130-2 with the gas in chamber 150. The gas pressure in the chamber 130-2 and tank 150 equalize at or around point [5] in graph 610. In one embodiment, the volume of chamber 130-2 and chamber 150 are approximately the same. In this example embodiment, opening of valve 160-5 causes the pressure in the chamber 130-2 to reduce by approximately 50%. The amount of reduction in pressure applied to chamber 130-2 varies depending on a volume of chamber 130-2 and a volume of chamber 150.

After another brief stabilization period (such as approx. 50 milliseconds or at point [6]), the controller 140 controls valve 160-4 (via generation of signal V4) to an open state to connect the chamber 130-2 (Left IPC) and the chamber 150 to the positive tank 170-1 to bring all three gas volumes up to the driving pressure again, during which the pressure in the chamber 130-2 causes the chamber 130-1 to pump respective fluid to the target recipient 108. Thus, embodiments herein include at least temporarily discontinuing application of the drive pressure in order to obtain pressure measurements at different times.

In one embodiment, the actual volume calculation produced by the controller 140 occurs based on measurements of pressure collected by the controller 140 at or around points [3], [4], and [5].

At substantially time T1 or point [3], the controller 140 receives signal P5 generated by pressure sensor 135-5 to determine the pressure Ppc of the gas applied to chamber 130-2.

At substantially time T1 or point [4], the controller 140 receives signal P3 generated by pressure sensor 135-3 to determine the pressure Pcom of the gas in chamber 150.

At substantially time T2 or point [5], the controller 140 receives signal P3 or P5 generated by pressure sensor 135-3 or pressure sensor 135-5 to determine the pressure Pmerge of the gas in chamber 150.

According to one embodiment, the controller 140 determines the volume of gas in chamber 130-2 using isothermal ideal gas laws as follows:

$$P_1 V_1 = P_2 V_2 \qquad \text{(equation 6)}$$

For:
$V_{pc}$=Unknown volume of the chamber 130-2 of diaphragm pump 130 (left IPC)
$V_{com}$=the known volume of the chamber 150 (Common Tank)
$P_{pc}$=pressure of the chamber 130-2 Left IPC at point [4]
$P_{com}$=pressure of the chamber 150 (Common Tank) at point [3]
$P_{merge}=P_{pc}=P_{com}$ pressure when the two chambers (130-2 and 150) are equalized at point [5]

$$V_{pc}P_{pc} + V_{com}P_{com} = V_{pc}P_{merge} + V_{com}P_{merge} \quad \text{(equation 7)}$$

$$\vdots$$

$$V_{pc} = V_{com}\frac{P_{merge} - P_{com}}{P_{pc} - P_{merge}} \quad \text{(equation 8)}$$

An isothermal calculation assumes that all transient thermal effects in the system have had time to dissipate. This dissipation can take on the order of seconds to occur, depending on the details of the system. If the volume calculation is performed prior to the system returning to thermal equilibrium, the residual temperature differences will introduce errors in the volume calculation, which will in turn cause errors in the resultant flow rate calculation.

In accordance with one embodiment, in order to achieve the range of flow rates required in an infusion pump system, and to minimize errors due to volume changes during the measurement cycle, the current embodiment can be configured to calculate a volume of fluid pumped to the target recipient 108 before the transient thermal effects have dissipated. In order to maintain volume calculation accuracy, embodiments herein take into account thermal effects to produce a more accurate fluid delivery rate.

In one embodiment, the temperature changes in the gas happen too fast to be measured by standard thermal sensors. In other words, thermal sensors may not be able to accurately measure fast changing temperatures of the gases in tank 150, chamber 130-2, etc., during a respective pressure changes shown in graph 600. To address this issue, one embodiment herein includes estimating temperatures of the volumes of interest to calculate an actual fluid delivery rate. As mentioned, the temperature sensor 152 measures an average temperature of gas in the common tank 150. However, due to its thermal mass, the temperature sensor 152 may not be able to accurately reflect an actual temperature of gas in chamber 150.

There are a number of parameters that affect the temperature of the gases in the different volumes (e.g., tank 150, chamber 130-2, etc.) over time. For example, thermal changes come primarily from 3 sources in the pneumatic system:

1. Adiabatic heating or cooling due to pressure changes in the chamber
2. Heat transfer between the gas and the chamber wall
3. Volume change due to flow rate out of the IPC chamber One embodiment herein includes modeling the fluid delivery system 100 to accurately estimate the temperature of the chambers of interest. For example, as mentioned, the change in pressure of chambers (such as pump chamber 130-2 and chamber 150) as shown and discussed with respect to FIG. 6 causes the temperature of the pump chamber 130-2 and the common tank 150 to vary. More specifically, between point 1 and point 2 in FIG. 6, the pressure of the common tank 150 drops significantly, causing the temperature of the gas, Tcom, in chamber 150 (common tank) to drop. As previously discussed, the pressure of gas in the respective chambers (e.g., P5, P3, etc.) is continuously and accurately measured using respective pressure sensors 135-5, 135-3, etc.

In one embodiment, a first model is used to estimate temperature changes in the chambers due to adiabatic heating and/or cooling. In other words, any suitable equations can be used to determine a change in the temperature of the gases in the chambers as a result of the pressures changing. Increasing a pressure of a gas causes an increase in temperature; decreasing a pressure of a gas causes a decrease in temperature.

Another parameter affecting the temperature of the gases in the chambers is the thermal characteristics of the chambers themselves and conduits in between. The dark lines in FIG. 2 represent conduits interconnecting the different components in fluid delivery system 100. For example, the dark line extending between diaphragm pump 130 and valve 160-5 represents a conduit; the dark line between valve 160-5 in chamber 150 represents a conduit; and so on. Via respective conduits, each of the components (such as check valve 125-1, diaphragm pump 130, valve 160-5, etc.) in fluid delivery system 100 are interconnected.

According to embodiments herein, the thermal properties of the chambers (e.g., common tank 150, pump chamber 130-2, etc.) can be characterized and modeled to identify how quickly they sink or source heat when there is a change in temperature caused by a change in pressure. As an example, and as discussed, the reduction in the pressure of a tank can cause the temperature of the gas in the tank to decrease. The temperature of the tank itself may be higher in magnitude than the temperature of the gas, resulting in a flow of heat from the tank or chamber to the gas therein. Thermal flow causes the temperature of the gas in the chamber to eventually become the substantially the same as the temperature in the respective tank over time. Conversely, an increase in pressure of the tank can cause the temperature to increase. The flow of heat from gas to the tank or chamber decreases the temperature of the gas.

One embodiment herein includes estimating the temperature of the gas and taking into account thermal heat flow using a respective thermal model. The thermal model takes into account the transfer of heat from the gas to the respective chamber or tank and/or a transfer of heat from the respective chamber or tank to the gas. The heat transfer will likely vary depending on the type of material used to fabricate the tanks and respective interconnections. Certain material such as metal will be more thermally conductive; material such as plastic will be less thermally conductive.

As discussed above, the changes in the temperature of the gases due to changes in pressure are deterministic and thus can be accurately estimated. However, the flow of energy from tank to gas or from gas to tank will impact the temperature. Embodiments herein include producing a more accurate estimate of temperature by taking into account these flows of energy at different times based on thermal modeling.

Another factor affecting the temperatures of the gases in the chambers is the volume of the pump chamber 130-2 and how quickly it changes over time due to pumping of the fluid in the diaphragm pump chamber to the target recipient. For example, if the fluid in the pump chamber 130-2 is pumped at a very slow rate to target recipient 108, then volume change effects are minor or potentially negligible. Conversely, if the fluid in pump chamber 130-1 is pumped at a relatively high rate to the target recipient 108, then the volume change effects become more significant. As discussed herein, embodiments herein take into account the volume changes.

In one embodiment, the controller 140 generates the estimation of temperatures at discrete points in time such as between one second and one nanosecond. For each time step (i.e., each discrete time of producing an estimation of temperature) of the control system, the change in temperature due to those three sources is calculated for each pneumatic volume using the measured pressure as an input. The components (e.g., adiabatic effects, heat transfer effects, volume change effects) can be measured individually and/or in combination to produce a respective estimated temperature.

In the following equations subscripts 'i' and 'j' are used to denote each of the pneumatic volumes 130-2, 150, 170-1, 170-2. The subscript 'i' represents the chamber for which the temperature is being estimated; the subscript 'j' represents the associated chamber. For example, when estimating a temperature for the pump chamber 130-2, the subscript 'i' represents the pump chamber 130-2; subscript 'j' represents the common tank 150. When estimating a temperature for the common tank 150, the subscript 'i' represents the common tank 150; subscript 'j' represents the pump chamber 130-2, and so on.

By way of a non-limiting example, the temperature at time (n+1) is then calculated based on that change rate:

$$\frac{dT_n}{dt} = \text{(Heat Transfer Effects)} + \text{(Pressure Change Effects)} + \text{(Volume Change Effects)} \quad \text{(equation 9)}$$

$$T_{n+1} = T_n + dt\frac{dT_n}{dt} \quad \text{(equation 10)}$$

Heat transfer effects are based on the temperature of the gas in the chamber, the temperature of the chamber wall, and the heat transfer coefficient between the two. For example, in one embodiment:

$$\text{Heat Transfer Effects } H(T_{wall} - T_i) \quad \text{(equation 11)}$$

$T_i$=last estimation of temperature for chamber i
H=heat transfer coefficient
$T_{wall}$=ambient temperature $T_{tc}$ as sensed by temperature sensor 152

Pressure change effects are based on the mass flow from once chamber to another due to pressure differential between the two chambers:

$$Q_{ij} = C_{ij}A_{ij}\sqrt{2\rho(P_i - P_j)} \quad \text{(equation 12)}$$

$$Q_{in} = \sum_j Q_{ji} \quad \text{(equation 13 and 14)}$$

$$Q_{out} = \sum_j Q_{ij}$$

Pressure Change Effects = (equation 15)

$$\frac{1}{M_i C_v}\left[C_p \sum_j T_j Q_{ji} - C_p T_i Q_{out} - C_v T_i (Q_{in} - Q_{out})\right]$$

Where:
$M_i$=mass of gas in chamber i;
$Q_{ij}$ is the mass flow rate from chamber i to chamber j.
$C_{ij}$ is the discharge coefficient of the valve between chamber i and j
$A_{ij}$ is the area of the orifice of the valve between chamber i and j
$\rho_i$ is the density of the gas in chamber i Volume change effects are based on any changes in actual volume of the chamber in question. In one embodiment, this effect only applies to chamber 130-2, which can change size due to motion of membrane 127.

$$\text{Volume Change Effects} = \left(\frac{C_p}{C_v} - 1\right)\cdot\frac{T_i}{V_i}\frac{dV_i}{dt} \quad \text{(equation 16)}$$

Where:
V=volume
Cv=specific heat at constant volume
Cp=specific heat at constant pressure The estimated temperature curves through the pumping and measurement cycles can be seen in FIGS. 5a, 5b, and 6.

In this method the control system has an estimated temperature for each gas chamber that can be used in a modified ideal gas law volume calculation that takes temperature into account:

$$V_{pc} = V_{com}\frac{\left(\frac{P_{com2}}{T_{com2}} - \frac{P_{com1}}{T_{com1}}\right)}{\left(\frac{P_{pc1}}{T_{pc1}} - \frac{P_{pc2}}{T_{pc2}}\right)} \quad \text{(equation 17)}$$

Where:
$V_{pc}$=Unknown volume of the chamber 130-2 of diaphragm pump 130 (e.g., Left IPC)
$V_{com}$=the known volume of the chamber 150
$P_{com1}$=pressure P3 from pressure sensor 135-3 of the chamber 150 at point [3]
$P_{com2}$=pressure P3 from pressure sensor 135-3 of the chamber 150 at point [5]
$P_{pc1}$=pressure P5 from pressure sensor 135-5 of the chamber 130-2 at point [4]
$P_{pc2}$=pressure P5 from pressure sensor 135-5 of the chamber 130-2 at point [5]
$T_{com1}$=estimated temperature of the chamber 150 at point [3A]
$T_{com2}$=estimated temperature of the chamber 150 at point [5A1]
$T_{pc1}$=estimated temperature of the chamber 130-2 at point [4A]
$T_{pc2}$=estimated temperature of the chamber 130-2 at point [5A2]

As previously discussed, the volume of the chamber 130-1 can be calculated by subtracting the calculated VPC (e.g., volume of the pumping chamber 130-2) from the total volume of the diaphragm pump 130. The total volume of the diaphragm pump 130 is equal to the volume of chamber 130-1 plus the volume of chamber 130-2 and is a known quantity.

In a further embodiment, the volume of chamber 130-1 is not calculated, and flow rate is calculated by simply taking the difference in volume between subsequent calculations of the volume of chamber 130-2. In other words, the change in volume of pump chamber 130-2 over time is indicative of a pumping flow rate and can be used as a basis to calculate the flow rate. The controller 140 can be configured to precisely determine a respective flow rate of delivering fluid from chamber 130—one of diaphragm pump 130 based on the multiple measurements taken at times C, D, E, etc., in FIG. 5b.

The flow rate=(change in volume of fluid in chamber 130-1)/(range of delivery time).

Using a temperature-corrected volume calculation (based on estimation of gas temperatures as described herein) allows the system to have a measure sequence that happens on the order of 80 milliseconds, rather than on the order of seconds while maintaining calculation accuracy.

Figure 7:
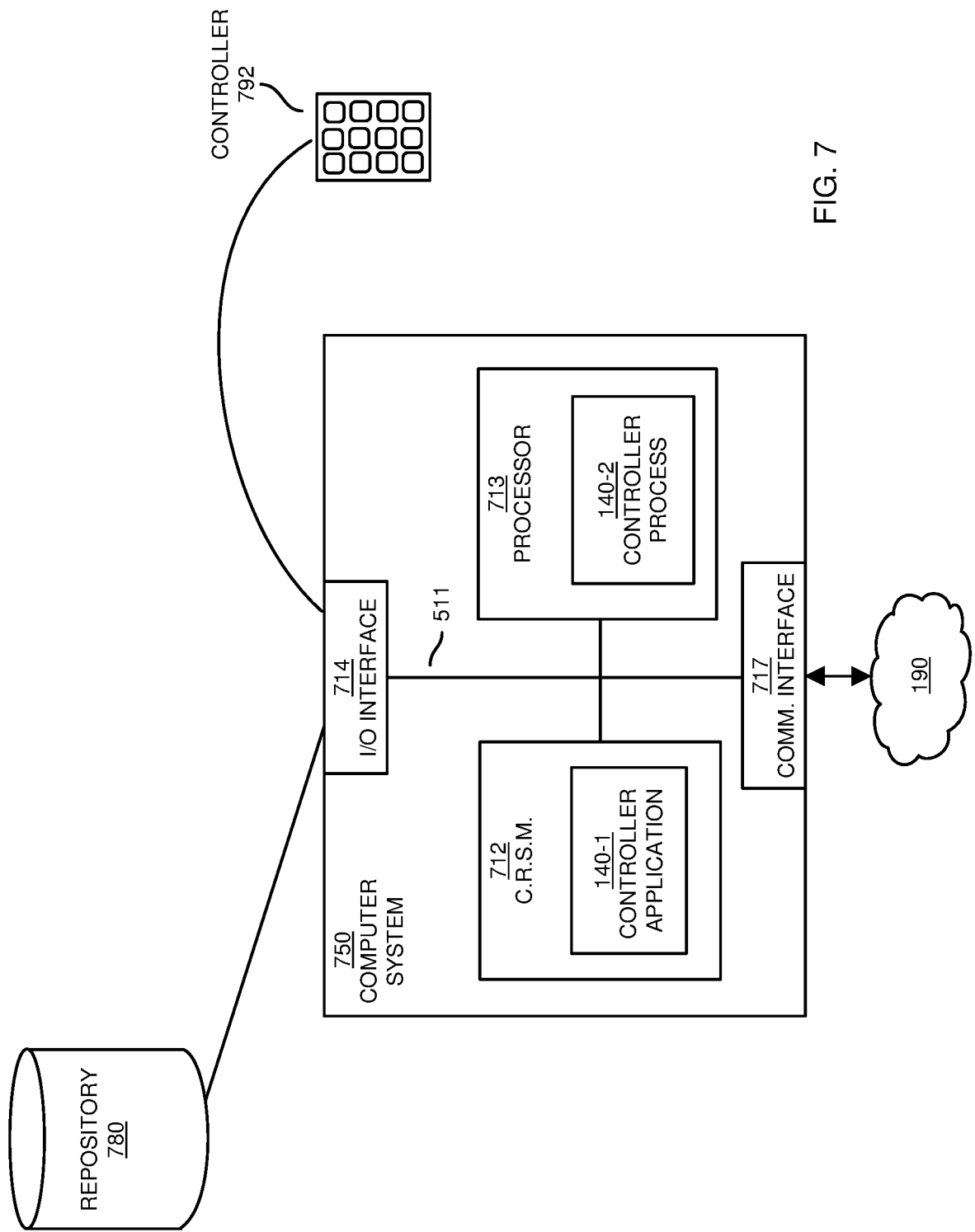
FIG. 7 is a diagram illustrating an example computer architecture in which to execute any of the functionality according to embodiments herein.

FIG. 7 is an example block diagram of a computer device for implementing any of the operations as discussed herein according to embodiments herein.

In one embodiment, fluid delivery system 100 includes a computer system 750 to execute controller 140.

As shown, computer system 750 of the present example includes an interconnect 711, a processor 713 (such as one or more processor devices, computer processor hardware, etc.), computer readable storage medium 712 (such as hardware storage to store data), I/O interface 714, and communications interface 717.

Interconnect 711 provides connectivity amongst processor 713, computer readable storage media 712, I/O interface 714, and communication interface 717.

I/O interface 714 provides connectivity to a repository 780 and, if present, other devices such as a playback device, display screen, input resource 792, a computer mouse, etc.

Computer readable storage medium 712 (such as a non-transitory hardware medium) can be any hardware storage resource or device such as memory, optical storage, hard drive, rotating disk, etc. In one embodiment, the computer readable storage medium 712 stores instructions executed by processor 713.

Communications interface 717 enables the computer system 750 and processor 713 to communicate over a resource such as network 190 to retrieve information from remote sources and communicate with other computers. I/O interface 714 enables processor 713 to retrieve stored information from repository 780.

As shown, computer readable storage media 712 is encoded with controller application 140-1 (e.g., software, firmware, etc.) executed by processor 713. Controller application 140-1 can be configured to include instructions to implement any of the operations as discussed herein.

During operation of one embodiment, processor 713 (e.g., computer processor hardware) accesses computer readable storage media 712 via the use of interconnect 711 in order to launch, run, execute, interpret or otherwise perform the instructions in controller application 140-1 stored on computer readable storage medium 712.

Execution of the controller application 140-1 produces processing functionality such as controller process 140-2 in processor 713. In other words, the controller process 140-2 associated with processor 713 represents one or more aspects of executing controller application 140-1 within or upon the processor 713 in the computer system 750.

Those skilled in the art will understand that the computer system 750 can include other processes and/or software and hardware components, such as an operating system that controls allocation and use of hardware resources to execute controller application 140-1.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 850 resides in fluid delivery system 100. However, note that computer system 850 may reside at any location or can be included in any suitable resource in network environment 100 to implement functionality as discussed herein.

Functionality supported by the different resources will now be discussed via flowcharts in FIGS. 8, 9, and 10. Note that the steps in the flowcharts below can be executed in any suitable order.

Figure 8:
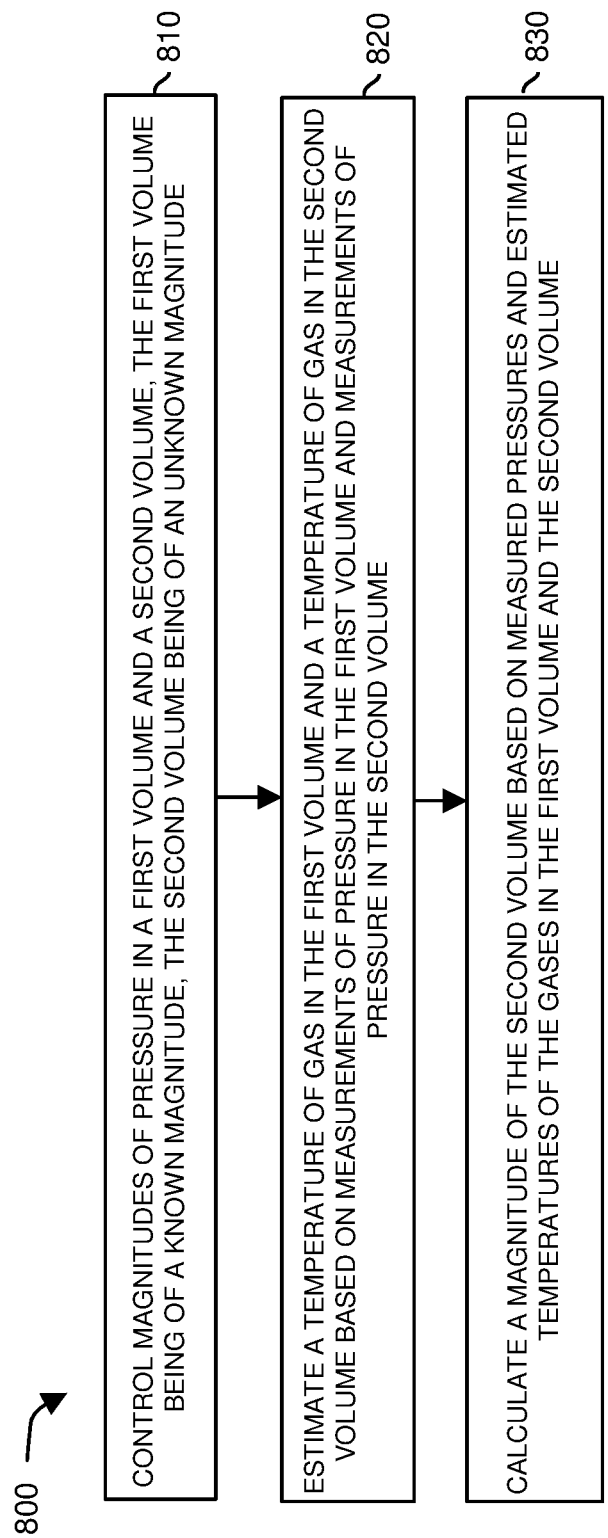
FIGS. 8–10 are example diagrams illustrating methods facilitating flow control measurement and management according to embodiments herein.

FIG. 8 is a flowchart 800 illustrating an example method according to embodiments. Note that there will be some overlap with respect to concepts as discussed above.

In processing block 810, the controller 140 controls magnitudes of pressure in a first volume (such as chamber 150) and a second volume (such as chamber 130-2). The first volume is of a known magnitude (i.e., size). The second volume is of an unknown magnitude (i.e., size).

In processing block 820, the controller 140 estimates a temperature of gas in the first volume and a temperature of gas in the second volume based on measurements of pressure in the first volume and measurements of pressure in the second volume.

In processing block 830, the controller 140 calculates a magnitude of the second volume based on measured pressures of the gases and estimated temperatures of gases in the first volume and the second volume.

Figure 9:
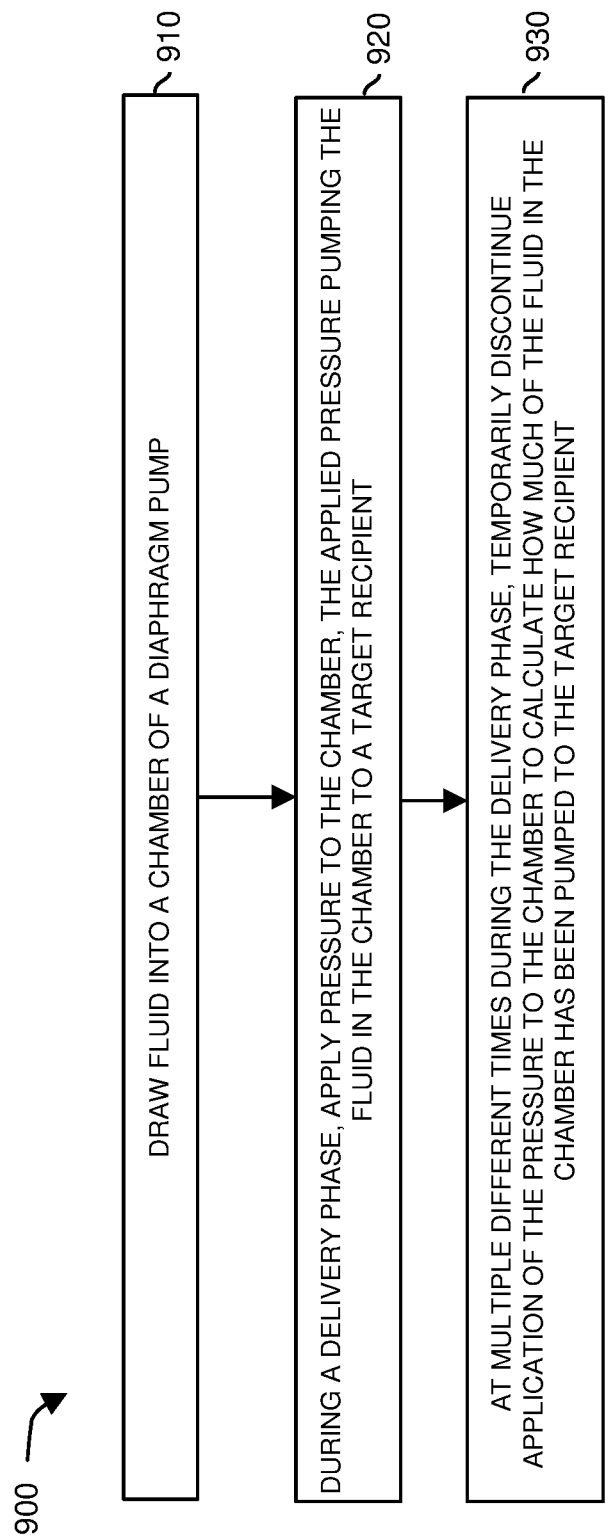

FIG. 9 is a flowchart 900 illustrating an example method according to embodiments. Note that there will be some overlap with respect to concepts as discussed above.

In processing block 910, the controller 140 draws fluid into a chamber of a diaphragm pump 130.

In processing block 920, during a delivery phase, the controller 140 applies pressure to the chamber 130-1. The applied pressure pumps the fluid in the chamber 130-1 to a target recipient 108.

In processing block 930, at multiple different times during the delivery phase, the controller 140 temporarily discontinues application of the pressure to the chamber 130-2 to calculate how much of the fluid in the chamber 130-1 has been pumped to the target recipient 108.

Figure 10:
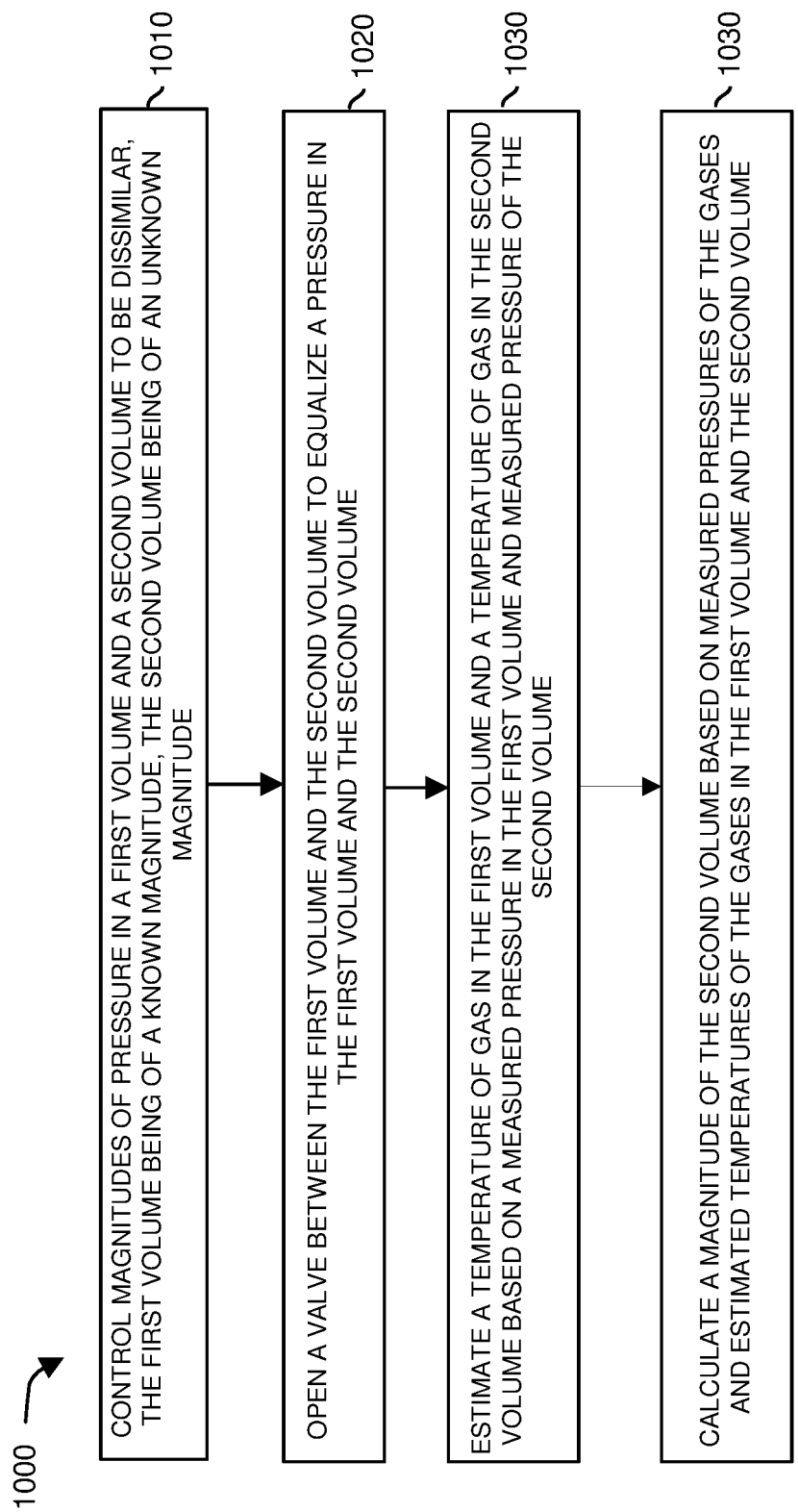

FIG. 10 is a flowchart 1000 illustrating an example method according to embodiments. Note that there will be some overlap with respect to concepts as discussed above.

In processing block 1010, the controller 140 controls magnitudes of pressure in a first volume (such as chamber 150) and a second volume (such as chamber 130-2) to be dissimilar. The first volume is of known magnitude. The second volume is of unknown magnitude.

In processing block 1020, the controller 140 initiates opening a valve 160-5 (while other valves are closed) between the first volume and the second volume to equalize a pressure in the first volume and the second volume.

In processing block 1030, the controller 140 estimates a temperature of gas in the first volume and a temperature of gas in the second volume based on a measured pressure in the first volume and measured pressure of the second volume.

In processing block 1040, the controller 140 calculates a magnitude of the second volume based on measured pressures of the gases and estimated temperatures of the gases in the first volume and the second volume.

As previously discussed, in one embodiment, a fluid delivery apparatus includes controller hardware, a diaphragm pump, a positive displacement pump, and a fluid conduit extending between the diaphragm pump and the positive displacement pump. During operation, and delivering fluid to a downstream recipient, the controller hardware draws fluid into a chamber of the diaphragm pump. The controller hardware applies pressure to the chamber of the diaphragm pump to output the fluid in the chamber of the diaphragm pump downstream through the fluid conduit to the positive displacement pump. A segment of the fluid conduit is an elastically deformable conduit driven by the positive displacement pump. During application of the pressure to the chamber and outputting the fluid in the chamber downstream, the controller hardware activates the positive displacement pump to pump the fluid in the segment from the positive displacement pump to the downstream recipient.

Figure 11:
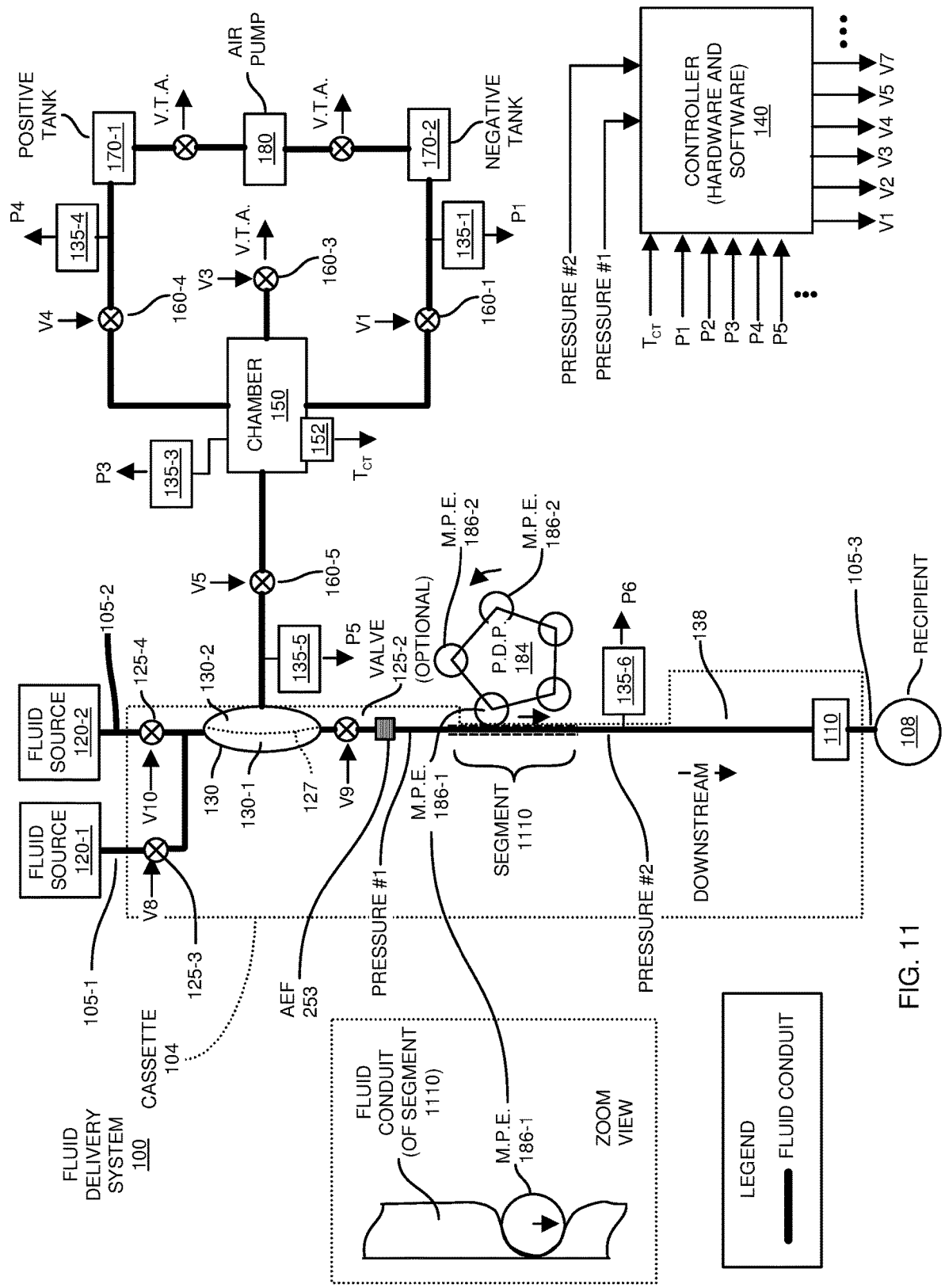
FIG. 11 is an example diagram of implementing a diaphragm pump and a positive displacement pump to deliver fluid to a respective recipient according to embodiments herein.

More specifically, FIG. 11 is an example diagram of implementing a diaphragm pump and a positive displacement pump to deliver fluid to a respective recipient according to embodiments herein.

More specifically, in accordance with one or more embodiments, a fluid delivery system (apparatus, device, etc.) includes controller 140 (hardware and/or software), a diaphragm pump 130, a positive displacement pump 184 (such as a peristaltic fluid pump, rotary lobe pump, progressive cavity pump, rotary gear pump, piston pump, diaphragm pump, screw pump, gear pump, hydraulic pump, rotary vane pump, rope pump, flexible impeller pump, etc.), and a fluid conduit (fluid conduit) extending between the diaphragm pump 130 through the positive displacement pump 184 to a recipient 108.

In one embodiment, the positive displacement pump is a non-pneumatically controlled pump such as a peristaltic fluid pump, rotary lobe pump, progressive cavity pump, rotary gear pump, piston pump, screw pump, gear pump, rotary vane pump, rope pump, flexible impeller pump, etc.). The diaphragm pump 130 is pneumatically (gas) driven and allows the controller to calculate flow rate as discussed herein.

In accordance with further embodiments, the positive displacement pump 184 can be another diaphragm pump (i.e., a pneumatically driven pump).

During operation of delivering fluid to the downstream recipient 108, the controller 140 initially draws fluid into a chamber 130-1 of the diaphragm pump 130 (such as via negative gas pressure applied to chamber 130-2). The fluid can be drawn into the chamber 130-1 from any suitable source.

For example, while valves 125-4 and 125-2 are closed, the controller 140 opens the valve 125-3. In such an instance, when negative pressure is applied to the chamber 130-2, the fluid pump 130 draws fluid from source 120-1 into the chamber 130-1. Conversely, while valves and 125-2 are closed, the controller 140 opens the valve 125-4. In such an instance, when negative pressure is applied to the chamber 130-2, the fluid pump 130 draws fluid from source 120-2 into the chamber 130-1.

Subsequent to filling the chamber 130-1 with fluid from one or both sources 120, the controller 140 closes the valves 125-3 and 125-4. As further discussed herein, the controller 140 opens valve 125-2 (if present) and applies a positive pressure to chamber 130-2, causing a flow of fluid out of the chamber 130-1 downstream to the fluid pump 184. As further discussed herein, the pinching of segment 1110 (as an alternative to closing valve 125-2) can be used to prevent backflow of fluid into the chamber 130-1 from the portion of conduit between the diaphragm pump 130 and the fluid pump 184 when drawing fluid from one or more source 120 into the chamber 130-1.

As further described herein, subsequent to filling the chamber 130-1 with fluid from fluid source 120-1, the controller 140 applies pressure to the chamber 130-1 of the diaphragm pump 130 to output the fluid in the chamber 130-1 (of the diaphragm pump 130) downstream through the fluid conduit to the positive displacement pump 184 (such as via positive gas pressure applied to chamber 130-2).

As shown, a segment 1110 of the fluid conduit of fluid delivery system 100 is an elastically deformable conduit (of any suitable material such as rubber, plastic, etc.) driven by the positive displacement pump 184. During application of the positive (gas) pressure to the chamber 130-1 (via filling chamber 130-2 with more and more gas over time) and outputting the fluid in the chamber 130-1 downstream to the positive displacement pump 184 through open valve 125-2 (if present), the controller 140 activates the positive displacement pump 184 to pump the fluid disposed in a portion of the segment 1110 downstream of the mechanical pump element 186-1 (such as a roller, peristaltic pump element, non-pneumatic pump element, or other suitable element to movably compress segment 1110) along the fluid conduit to the downstream recipient 108.

Accordingly, in one embodiment, a diaphragm pump 130 delivers fluid to the elastically deformable conduit (segment 1110); the controller 140 controls the positive displacement pump 184 and corresponding mechanical pump element 186-1 in a sweeping motion (in a downward direction in FIG. 2) to deliver the fluid in the segment 1110 in a downstream direction to recipient 108.

More specifically, as shown, in one embodiment, the mechanical pump element 186-1 is in contact with and pinches or obstructs the elastically deformable conduit at position #1. Via the pinching, while at rest, the mechanical pump element 186-1 blocks a flow of fluid from the diaphragm pump 130 further downstream of position #1 into a portion of the segment 1110 downstream of the mechanical pump element 186-1.

Sweeping physical contact of the mechanical pump element 186-1 to the elastically deformable conduit controllably conveys fluid in the elastically deformable conduit further downstream to the recipient 108. Accordingly, in one embodiment, the mechanical pump element 186-1 performs multiple operations including: i) restricting (or holding back) a flow of the fluid received upstream of the mechanical pump element 186-1 from the diaphragm pump 130 into the segment 1110 (elastically deformable conduit) as well as ii) via the positive displacement pump 184, controlling delivery of fluid in the segment (elastically deformable conduit) downstream of the mechanical pump element 186-1 to the recipient 108 (such as a person, animal, machine, etc.).

In accordance with further embodiments, a pressure (pressure #1) of the fluid upstream of the mechanical pump element 186-1 is different than a pressure (pressure #2) of the fluid downstream of the mechanical pump element 186-1. More specifically, in one embodiment, during pumping of fluid downstream from the diaphragm pump 130 to the positive displacement pump 184 through open valve 125-2 (if present), a pressure #1 of the fluid in a first portion of the fluid conduit upstream of the mechanical pump element 186-1 (which blocks a flow of the fluid via pinching or obstructing of the fluid conduit that conveys the fluid) is greater than a pressure (pressure #2) of fluid in a second portion of the fluid conduit downstream of the mechanical pump element 186-1.

Conversely, in certain instances of pumping, the recipient 108 may apply backpressure on the fluid delivered through tube 105-3. In such an instance, the pressure #1 of the fluid in a respective portion of the fluid conduit upstream of the mechanical pump element 186-1 (which blocks a flow of the fluid via pinching/obstructing of the fluid conduit that conveys the fluid) is less than a pressure (pressure #2) of fluid in a second portion of the fluid conduit downstream of the mechanical pump element 186-1. For example, while the positive displacement pump 184 pumps fluid, the recipient 108 may provide backpressure to receiving fluid from a respective outlet of fluid pathway through tube 105-3.

In accordance with another embodiment, the controller 140 of the fluid delivery apparatus as described herein is further operable to: measure (in any suitable manner) a rate of fluid expelled from the chamber 130-1 of the diaphragm pump 130 downstream to the segment of fluid conduit using techniques as discussed in subsequent FIGS. 9-15 and text. In such an instance, the controller 140 uses measured rate of expelled fluid from the chamber 130-1 downstream through the open valve 125-2 (if present) to the positive displacement pump 184 over each of multiple measurement windows (shown as measurement D, measurement E, measurement F, measurement G, measurement age, in FIG. 10A; an example of a respective measurement window is shown in FIG. 11) to control a rate of moving the mechanical pump element 186-1 to deliver the fluid to the recipient at a desired flow rate. In such an embodiment, the diaphragm pump 130 serves as an accurate way of measuring fluid delivered by the positive displacement pump 184 to the respective recipient 108.

Note that a rate of operating diaphragm pump 130 (pneumatic pump) and positive displacement pump 184 can be synchronized such that the diaphragm pump 130 delivers fluid to the segment 1110 at a substantially similar rate as the positive displacement pump 184 delivers fluid in segment 1110 downstream to the recipient 108.

As further discussed below, note that the fluid flow rate of fluid through the diaphragm pump 130 can be measured using conventional algorithms known in the art based on ideal gas laws. For example, in one embodiment, the controller 140 is further operable to: cyclically receive (draw), over each of multiple fill cycles, a quantum of the fluid from a disparately located fluid source container (such as fluid source 120-1) into the chamber 130-1 of the diaphragm pump 130 at each of multiple fill times. After each fill, as previously discussed, the controller 140 fills the chamber 130-2 with gas, which applies positive pressure to the chamber 130-1. As previously discussed, the membrane 130-1 separates the fluid in chamber 130-1 from the gas in chamber 130-2.

As previously discussed, in one embodiment, fluid delivery system 100 includes valve 125-2 (such as a fully OPEN or fully closed valve in this case); an OPEN/CLOSED setting of valve 125-2 is controlled by signal V9 generated by controller 140.

In accordance with further embodiments, note that the controller 140 can be configured to control the valve 125-2 disposed between the first fluid pump 130 and the second fluid pump (such as positive displacement pump 184) to control flow in any manner. For example, control of the valve 125-2 allows selective flow of the fluid (such as fluid from sources 120-1 or 120-2 or both) from the first fluid pump through the second fluid pump to a recipient 108. More specifically, closing valve 125-2 prevents a flow of fluid from the fluid pump 130 to the fluid pump 184. Conversely, opening of the valve 125-2 enables a flow of fluid from the fluid pump 130 to the fluid pump 130 to the fluid pump 184.

Thus, the controller controls flow of fluid via 3 components including the fluid pump 130, valve 125-2, and the positive displacement pump 184 disposed in a respective fluid pathway (conduit).

As previously discussed, note again that valve 125-2 is optional. That is, at least one of the mechanical pump elements 186 can be configured to pinch or obstruct the segment 1110 and prevent a flow of fluid through segment 1110 at any or all times. For example, embodiments herein include discontinuing counterclockwise rotation of the positive displacement pump 184 to purposefully block a flow of fluid from the first fluid pump 130 through the fluid pump 184 to the recipient 108.

As further shown, the fluid delivery system 100 can be configured to include an air elimination filter 253 disposed in between the fluid pump 130 and the positive displacement pump 184. In one embodiment, while the valve 125-2 is OPEN via an appropriate setting of control signal V9, and while segment 110 is simultaneously pinched resulting in an obstruction of flow of fluid from the fluid pump 130 through the positive displacement pump 184 to the recipient 108, due to pressure #1 (such as a pressure greater than atmospheric pressure), any gas present in the fluid conduit between the fluid pump 130 and the positive displacement pump 184 is expelled to atmosphere via the air elimination filter 253 as the respective flows through the respective conduit.

Thus, the air elimination filter 253 removes unwanted gas from the flowing fluid via pressure #1 (such as a pressure greater than atmospheric pressure); the fluid in the fluid conduit passes through the air elimination filter 253 downstream to the fluid pump 184 for subsequent delivery in a manner as discussed herein.

Figure 12:
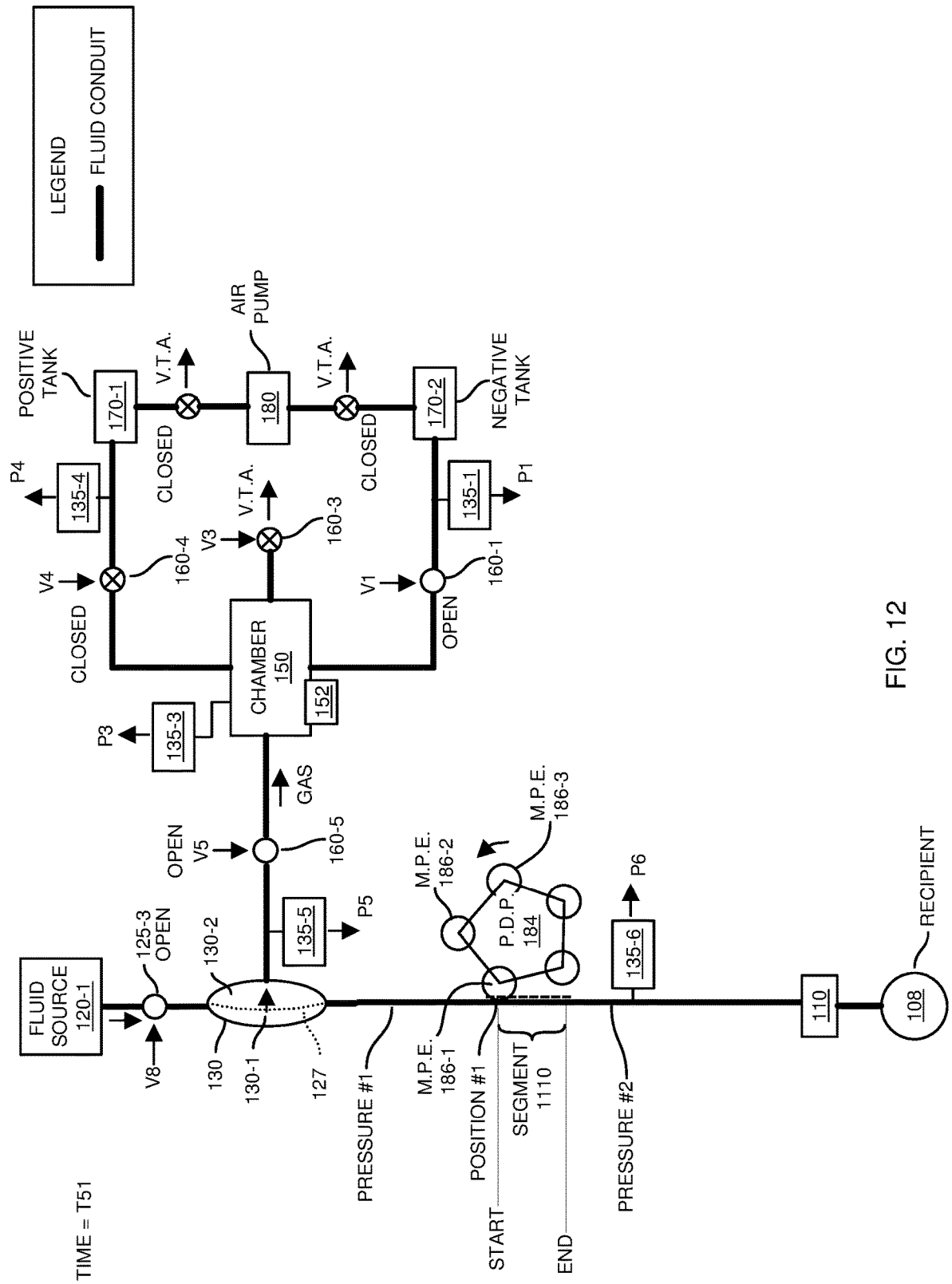
FIG. 12 is an example diagram illustrating drawing of fluid from a respective fluid source into a chamber of a diaphragm pump according to embodiments herein.

FIG. 12 is an example diagram illustrating drawing of fluid from a respective fluid source into a chamber of a diaphragm pump according to embodiments herein.

As previously discussed, the controller 140 produces respective control signals to control states of the valves to either open or closed positions. In one embodiment, while the valve 125-3 (a controllable full open or full closed valve in this embodiment) is open, valve 160-5 is open, valve 160-1 is open, while valves 160-4 and 160-7 are closed, the controller 140 applies a negative pressure to the chamber 130-2 of the diaphragm pump 130. This evacuates gas from the chamber 130-2, causing the membrane 127 to draw the fluid from the fluid source 120-1 (fluid container) into chamber 130-1.

Accordingly, embodiments herein include controlling the flow of fluid from different fluid sources 120-1 and 120-2 into the first fluid pump 130-1.

If desired, the controller 140 draws the fluid from the fluid source 120-1 into the chamber 130-1 of the diaphragm pump 130 during a condition in which mechanical pump element 186-1 of the positive displacement pump 184 blocks a flow of any downstream fluid being pulled backwards into the chamber 130-1. In other words, the mechanical pump element 186-1 acts as a valve in a closed position as shown in FIG. 3. Thus, instead of drawing fluid from further downstream of the elastically deformable conduit into the chamber 130-1, the application of the negative pressure to the chamber 130-2 causes the diaphragm pump 130 to draw only the fluid from the upstream fluid source 120-1 into the chamber 130-1. As previously discussed, valve 125-2 in FIG. 2 is optional.

Figure 13:
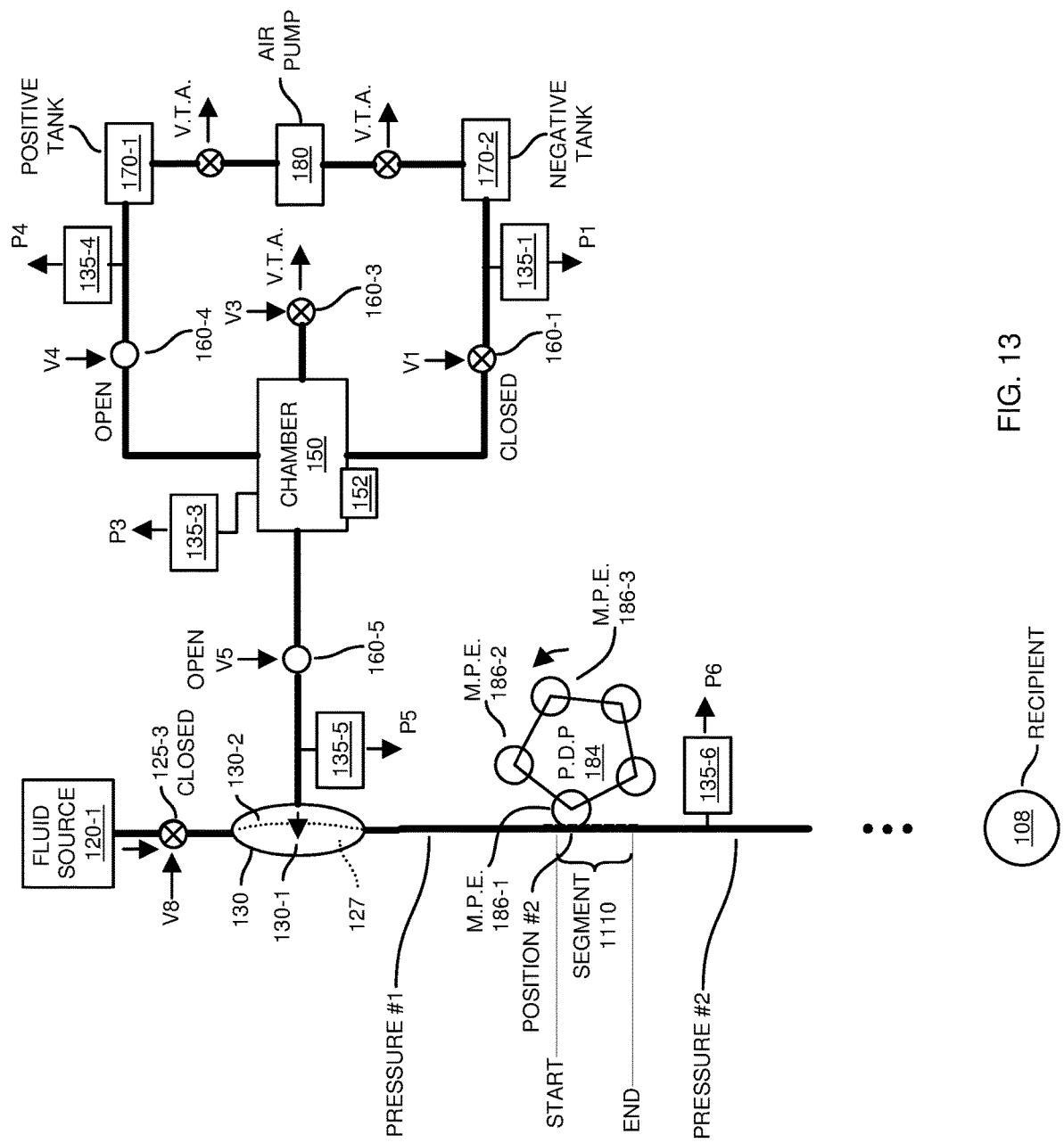
FIG. 13 is an example diagram illustrating application of positive pressure to the chamber of the diaphragm pump to convey fluid to a respective downstream positive displacement pump according to embodiments herein.

FIG. 13 is an example diagram illustrating application of positive pressure to the chamber of the diaphragm pump to convey fluid to a respective downstream positive displacement pump according to embodiments herein.

As previously discussed, subsequent to drawing the fluid into the chamber 130-1 of the diaphragm pump 130, the controller 140 closes valve 125-3 and valve 160-1 (via generation of respective control signals V8 and V1); the controller 140 opens valve 160-5 and valve 160-4 (via generation of respective control signals V5 and V4) to apply a positive gas pressure to the chamber 130-1 of the diaphragm pump 130 to deliver the fluid in the chamber 130-1 downstream to the positive displacement pump 184.

As shown, during application of positive pressure to the fluid in chamber 130-1, the mechanical pump element 186-1 of the positive displacement pump 184 controls a rate at which fluid from the diaphragm pump 130 is allowed to flow downstream into the segment 1110. As previously discussed, in addition to controlling an amount of fluid received in segment 1110 upstream of the mechanical pump element 186-1, the movement of the mechanical pump element 186-1 (in a downward direction) also controls the rate of delivering respective fluid in the segment 1110 to the recipient 108.

As previously discussed, the controller can be configured to synchronously operate rate of the diaphragm pump and positive displacement pump 184 such that the diaphragm pump 130 delivers fluid to the segment 1110 at a substantially similar rate as the positive displacement pump 184 delivers fluid in segment 1110 downstream to the recipient 108.

Figure 14:
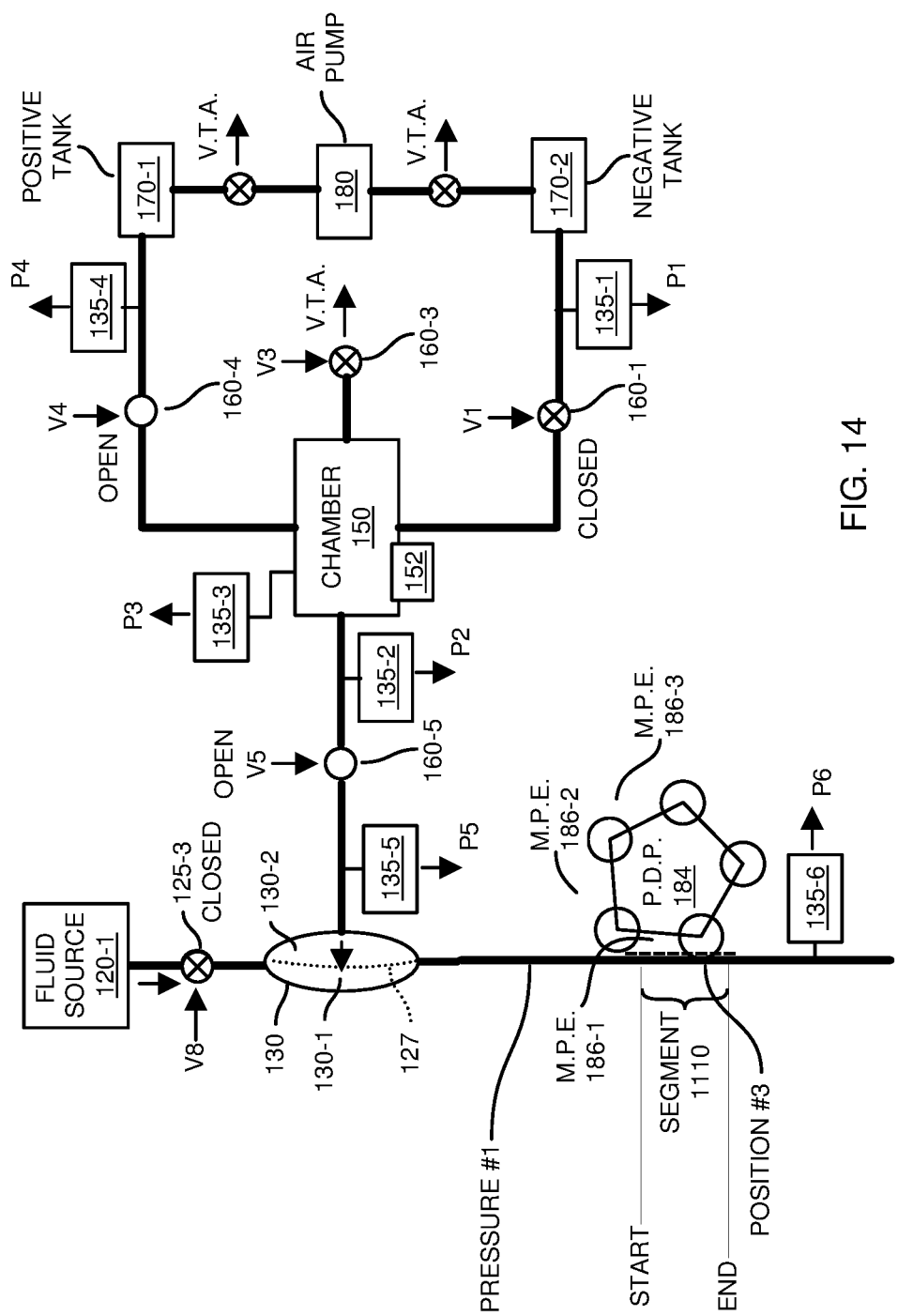
FIG. 14 is an example diagram illustrating motion of a mechanical pump element to deliver fluid (as received from a diaphragm pump) to a downstream recipient according to embodiments herein.

FIG. 14 is an example diagram illustrating continued motion of a mechanical pump element while receiving fluid from a diaphragm pump according to embodiments herein.

As shown, the positive displacement pump 184 can be configured to continue to rotate over time about a respective axis (center of mechanical pump elements 186) such that when the mechanical pump element 186-1 reaches the end of the segment 1110, the next mechanical pump element 186-2 contacts the start location of segment 1110 to pinch or obstruct the segment 1110. This sets up the mechanical pump element 186-1 of the positive displacement pump 184 to start location of segment 1110. This starts a new cycle of sweeping the mechanical pump element 186-2 along segment 1110 to deliver fluid to the respective recipient 108. As previously discussed, in one embodiment, at least one of the mechanical pump elements 186 always pinches, occludes, compresses, obstructs, etc., the segment 1110 to prevent backflow of fluid from the segment 1110 to the diaphragm pump 130. Hence, valve 125-2 may not be needed.

Note that the positive displacement pump 184 (a positive displacement pump) can be any type of peristaltic mechanism (rotary, linear, piston, etc.) as long as the downstream pump segment 1110 is never allowed to open and allow free flow of fluid from the diaphragm pump 130 to the recipient 108. In other words, in one embodiment, the positive displacement pump or its corresponding elements (such as mechanical pump elements 186-1, 186-2, etc.) can be configured to always occlude a flow of the fluid from the diaphragm pump 130 downstream to the recipient 108. In such an instance, the positive displacement pump 184 constantly controls the flow of fluid to the recipient 108.

Note that the ratio of volume of fluid drawn into the chamber 130-1 may be substantially the same or different than the volume of fluid in segment 1110. Accordingly, to empty all of the fluid stored in chamber 130-1 may require: i) a single cycle of sweeping a mechanical pump element 186-1 along the segment 1110, ii) less than a single cycle of sweeping a mechanical pump element 186-1 along the segment 1110, or iii) multiple cycles of sweeping mechanical pump elements along the segment 1110.

Further, if desired, the positive displacement pump 184 can be operated in a continuous manner to provide a continuous flow of fluid to the respective recipient 108 even though the controller 140 occasionally or periodically initiates refilling of the chamber 130-1 during the continuous flow and movement of the mechanical pump elements 186.

Alternatively, if desired, the controller 140 can be configured to discontinue operation of the positive displacement pump 184 during a condition in which the chamber 130-1 is refilled with fluid from fluid source 120-1.

In accordance with further embodiments, the controller 140 can be configured to stop (halt) movement of the positive displacement pump 184 and corresponding one or more pump elements in contact with the segment 1110. While the pump element is stopped, the controller 140 temporarily adjusts the pressure applied to the chamber of the diaphragm pump to measure a respective portion of fluid remaining in the diaphragm pump in a manner as previously discussed. Thus, if desired, embodiments herein can include pausing the positive displacement pumping mechanism to discontinue flow of fluid from the positive displacement pump 184 to the recipient 108 during instances when the amount of fluid remaining in the chamber 130-1 is being measured in a respective sample window.

Figure 15:
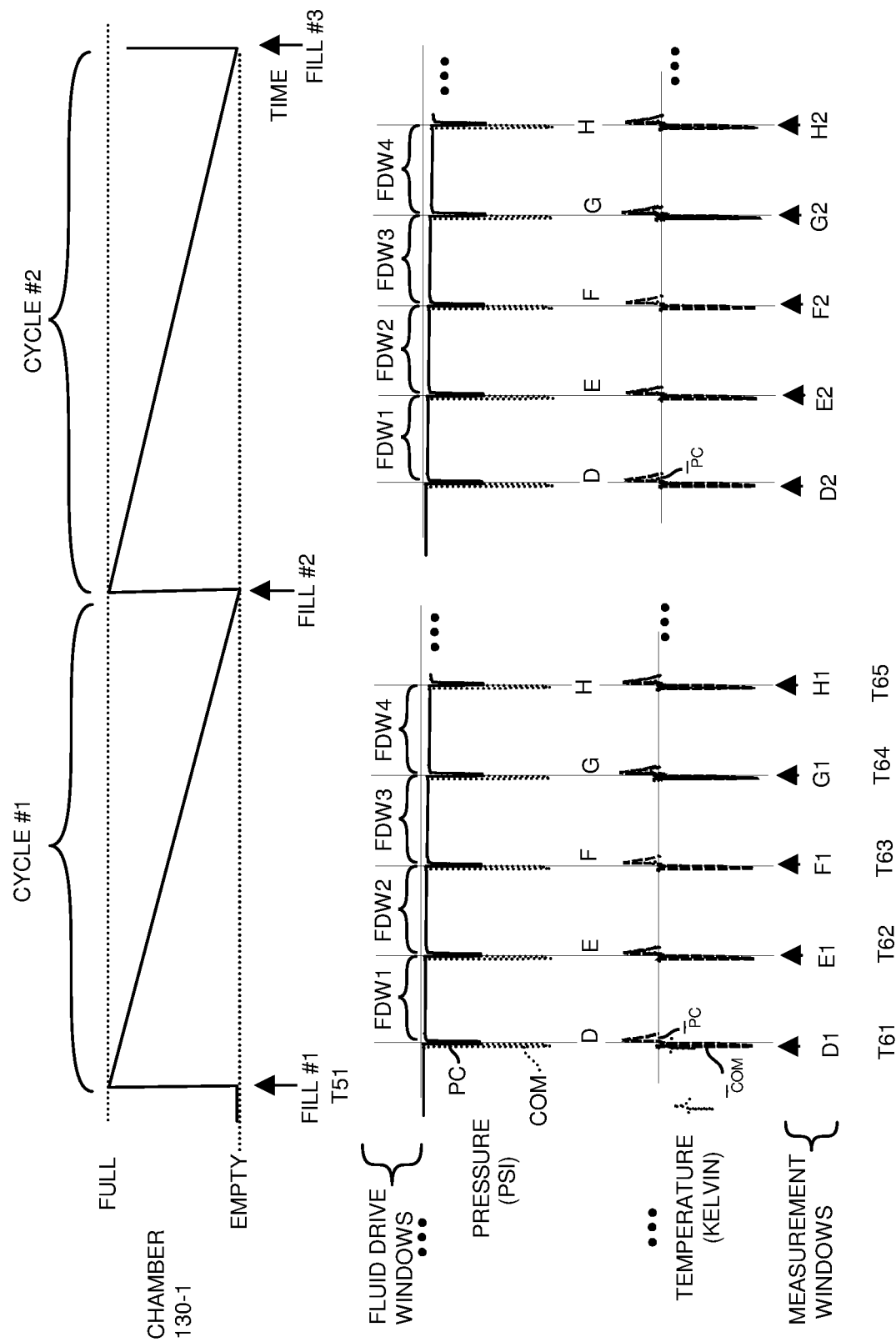
FIG. 15 is an example timing diagram illustrating timing windows associated with multiple pump cycles and multiple measurement windows within each cycle according to embodiments herein.

FIG. 15 is an example timing diagram illustrating multiple measurement windows within each pump cycle according to embodiments herein.

In accordance with embodiments herein, during FILL #1, in a manner as previously discussed, the controller 140 applies negative pressure to the chamber 130-2 and chamber 130-1 while valve 125-3 is open, and while mechanical pump element 186-1 obstructs fluid flow and prevents backflow of fluid in segment 1110 to chamber 130-1. During FILL #2, a next successive time of filling chamber 130-1, the controller 140 applies negative pressure again to the chamber 130-2 while valve V8 is open, and while mechanical pump element 186-1 prevents backflow of fluid in segment 1110 to chamber 130-1.

At each of multiple measurement times between a first time of filling FILL #1 and next filling FILL #2, the controller 140 temporarily adjusts application and a magnitude of the applied positive pressure to chamber 130-1 in between windows (fluid drive windows FDW1, FDW2, FDW3, FDW4, etc.), which occur between fill times FILL #1 and FILL #2.

Interrupting application of pressure (while valve 125-3 controlled by signal V8 is closed) can include temporarily changing the gas pressure from chamber 130-2 at each of multiple windows D1, E1, F1, G1, H1, etc.) to measure an amount of fluid remaining in chamber 130-1 at respective times T61, T62, T63, T64, T65, etc.

The controller 140 uses the measured amount of fluid in the chamber 130-1 at multiple sample times to derive a rate of delivering the fluid from the chamber 130-1 downstream to the segment 1110. For example, the chamber may hold 0.5 ml (milliliters) of fluid following FILL #1. Assume that measurement in window FDW1 around time T61 indicates 0.5 ml in the chamber; measurement in window FDW2 around time T62 indicates 0.4 ml in the chamber; measurement in window FDW3 around time T63 indicates 0.3 ml in the chamber; measurement in window FDW4 around time T64 indicates 0.2 ml in the chamber; and so on. If the measurement windows are spaced apart by 4 seconds, then the controller 140 determines the rate of flow through the diaphragm pump 184 to be 0.3 ml/12 Seconds=90 milliliters per hour.

In accordance with more specific embodiments, the controller 140 further controls the mechanical pump element 186-1 in contact with the segment 1110 of fluid conduit to continuously move along a length of the segment 1110 (such as even during FILL #1, FILL #2, etc.) to provide corresponding continuous flow of fluid from the segment 1110 to the recipient 108 in a respective delivery window.

As previously discussed, during each of multiple measurement windows (D1, E1, F1, G1, H1, for cycle #1, D2, E2, F2, G2, H2, for cycle #2, etc.) of interrupting application of the pressure within the delivery window, the controller 140 measures a respective portion of fluid remaining in the diaphragm pump 130. Note again that details of measuring the amount of fluid in chamber 130-1 are discussed above in FIG. 10A as well as elsewhere throughout this specification.

The controller 140 utilizes the respective measured portions of fluid remaining in the diaphragm pump 130 as measured during the multiple measurement windows (D1, E1, F1, G1, H1, for cycle #1, D2, E2, F2, G2, H2, for cycle #2, etc.) to calculate a rate of fluid delivered by the positive displacement pump 184 to the recipient 108. In the above example, as previously discussed, the controller 140 determines the rate of flow through the diaphragm pump 184 to be 0.3 ml/12 Seconds=90 milliliters per hour. This indicates that the rate of fluid delivered by the positive displacement pump 184 is 90 milliliters per hour. Accordingly, the controller 140 utilizes the respective measured portions of fluid remaining in the chamber 130-1 of the diaphragm pump 130 as measured during the multiple measurement windows (such as between one or more full to empty states) to calculate a rate of fluid delivered by the positive displacement pump 184 to the recipient 108.

As further discussed below, the controller 140 can be configured to use the measured flow rate to control operation of the positive displacement pump 184 such that the positive displacement pump 184 delivers fluid to the recipient at a desired rate. For example, as further discussed below, if the flow rate of delivering fluids as indicated by measurements of the chamber 130-1 over time is less than a desired rate, the controller 140 increases a rate of moving the mechanical pump element 186-1 along segment 1110 to increase the rate of fluid flow to recipient 108. Conversely, if the flow rate of delivering fluids as indicated by measurements of the chamber 130-1 over time is greater than a desired rate, the controller 140 decreases a rate of moving the mechanical pump element 186-1 along segment 1110 to decrease the rate of fluid flow to recipient 108.

FIG. 16 is an example diagram illustrating control of a respective positive displacement pump based upon a calculated fluid flow rate of fluid delivered by a respective diaphragm pump according to embodiments herein.

As previously discussed, to provide precise fluid flow control over a large possible range, the controller 140 measures a flow rate of fluid delivered to the recipient 108 based upon measurements of a respective remaining portion of fluid in the chamber 130-1 over each of multiple sample times (such as measurement windows D1, E1, F1, G1, H1, for cycle #1; measurement windows D2, E2, F2, G2, H2, for cycle #2, etc.).

In one embodiment, as shown, the controller 140 includes diaphragm pump interface 1640. In a manner as previously discussed, the diaphragm pump interface 1640 is operable to measure a flow rate of the fluid expelled from the chamber 130-1 of the diaphragm pump 130 downstream to the segment 1110 of the fluid conduit. As mentioned, techniques of measuring the flow rate are discussed in FIGS. 9-15. In general, calculation of a flow rate of delivering the fluid from the fluid pump 130 through the conduit to the fluid pump 184 is based on multiple calculated remaining amounts of fluid in the chamber 130 of the fluid pump 130 between a filled-with-fluid state and an empty-state of the chamber 130-1.

During operation, the diaphragm pump interface 1640 produces signal 1630 (feedback) indicating the calculated fluid flow rate from diaphragm pump 130 downstream to the positive displacement pump 184. The flow rate of fluid through the diaphragm pump 130 is generally (with slight variations over time) the same flow rate that the positive displacement pump 184 delivers fluid downstream to the recipient 108.

In accordance with further embodiments, the controller 140 utilizes the measured flow rate of the fluid (as detected from measuring respective remaining portions of fluid in the chamber 130-1 of the diaphragm pump 130 over multiple sample times T61, T62, T63, T64, etc.) to control (adjust) a sweep rate of moving the mechanical pump elements 186 along the segment 1110 of the fluid conduit to provide delivery of fluid from the positive displacement pump (and corresponding elastically deformable conduit) to the recipient 108 as specified by a desired flow rate setting (such as a user selected rate).

For example, the difference logic 1620 produces a respective flow error signal 1660 indicating a difference between the calculated fluid flow rate as indicated by signal 1630 (as measured from the diaphragm pump 130) and the target flow rate 1610.

If the measurement of fluid flowing through the diaphragm pump 130 (as measured over time) is greater than the desired flow rate setting, resulting in a positive flow error signal 1660, the positive displacement pump speed controller 1650 of the controller 140 decreases a current rate of sweeping the mechanical pump element 186-1 along segment 1110. Conversely, if the measurement of the fluid flowing through the diaphragm pump 130 as detected by the controller 140 is less than the desired flow rate setting, resulting in a negative flow error signal 1660, the peristaltic pump speed controller 1650 of controller 140 increases the rate of sweeping the mechanical pump element 186-1.

If desired, the controller 140 can be configured to monitor a magnitude of pressure #1 to verify that there is no backup of fluid between the diaphragm pump 130 and the positive displacement pump 184.

In this manner, the controller 140 uses the flow error signal 1660 to control the fluid flow to the target flow rate 1610. That is, via pump speed controller 1650, the controller 140 controls the flow of fluid from the fluid pump 184 based on feedback (flow rate signal 1630) indicating a rate at which the fluid pump 130 delivers the fluid from source 120-1 or 120-2 or both through conduit to the recipient 108. Accordingly, in one embodiment, the measured rate of fluid flow through the diaphragm pump 130 can be used as a basis to control the downstream peristaltic pump 184 to provide very accurate fluid flow over a large range.

In yet further embodiments, because the fluid pump 184 determines a rate of the fluid delivered to a respective recipient, the control of the fluid pump 184 is a primary manner of controlling a rate of fluid flowing through a combination of the fluid pump 130 and fluid pump 184 to the recipient. In other words, the controller 140 controls a rate of fluid flowing through the fluid pump 130 via operation of the second fluid pump 184.

As further example, between time T61 and time T64, assume that the controller 140 is controlling the mechanical pump element 186-1 to move along segment 1110 at a linear rate of 2.0 millimeters per second, which resulted in a measured flow rate of 90 milliliters per hour as indicated above. The controller 140 uses the measured rate of fluid flow through the fluid pump 130 to control a rate of operating the fluid pump 184. For example, if the target flow rate is 108 milliliters per hour, based on the measured rate of fluid flow as indicated by signal 1630, the error signal 1660 indicates—18 milliliters per hour. To deliver fluid at an appropriate rate of 108 milliliters per hour, the controller 140 increases a rate of moving the mechanical pump element 186-1 (and corresponding elements 186) to a rate of 2.4 millimeters per second along segment 1110. Thus, embodiments herein include controlling delivery of fluid from the fluid pump 184 to the recipient 108 at a flow rate as specified by a flow rate setting such as 108 milliliters per hour.

As previously discussed, the unique fluid delivery apparatus including a diaphragm pump 130 (to measure a fluid delivery rate) and a positive displacement pump 184 (to control physical pumping of fluid to a recipient 108) provides advantageous delivery of fluid in comparison to conventional techniques. For example, the fluid delivery apparatus and corresponding methods as described herein provide one or more of the following advantages over conventional techniques: i) fast start and stop time to reach desired delivery flow rate set point, ii) large dynamic range to control flow rates from 0.1 or lower to 1200 or higher, iii) flow rate control that is immune to inlet or outlet pressure changes, iv) flow rate control that is immune to large variations in fluid properties (such as viscosity), and so on. Also, note that variation in size of the tubing due to manufacturing tolerances and variation in contained volume in the tubing due to wear during operation can cause variation in flow output.

Additionally, application of positive pressure to the diaphragm pump as discussed herein provides feeds fluid to a positive displacement pump, resulting in better flow continuity. Additionally, the diaphragm pump is operable to draw fluid using negative pressure. In such an instance, the diaphragm pump can draw fluid from a container source disposed lower in elevation than the diaphragm pump.

Accordingly, embodiments herein include drawing fluid into a chamber 130-1 of the first fluid pump 130. The controller 140 operates the first fluid pump 130 to output the fluid in the chamber 130-1 of the first pump 130 downstream through a respective conduit to the fluid pump 184. Via the diaphragm pump interface 1640, the controller 140 measures delivery of fluid (from fluid source 120-1 or 120-2) to the fluid pump 184. Yet further, during operation of the fluid pump 130 and pumping of respective fluid downstream to the fluid pump 184, the controller 140 activates operation of the second fluid pump 184. Activation of the second fluid pump 184 pumps the fluid received from the fluid pump 130 to a recipient 108.

FIG. 17 is an example diagram illustrating a method of delivering fluid to a respective recipient using a combination of a diaphragm pump and a peristaltic pump according to embodiments herein.

In processing operation 1710 of flowchart 1700, the controller 140 (hardware and/or executed instructions of software) draws fluid from fluid source 120-1 into chamber 130-1 of the diaphragm pump 130.

In processing operation 1720, the controller 140 applies pressure to the chamber 130-1 of the diaphragm pump 130 to output the fluid in the chamber 130-1 of the diaphragm pump 130 downstream through a fluid conduit to positive displacement pump 184.

In processing operation 1730, during application of the pressure to fluid in the chamber 130-1 and outputting the fluid from the chamber downstream to the positive displacement pump 84, the controller 140 activates operation of the positive displacement pump 184 to pump the fluid from the positive displacement pump 184 to a recipient 108.

Note again that techniques herein are well suited for use in fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
   applying a drive pressure to fluid in a chamber of a diaphragm pump, the applied drive pressure causing flow of the fluid out of the chamber in a downstream direction from the diaphragm pump through a conduit;
   temporarily discontinuing application of the drive pressure to the chamber to calculate a portion of the fluid remaining in the chamber; and
   resuming application of the drive pressure to the chamber, the resumed application of drive pressure causing resumed flow of the remaining fluid from the chamber through the conduit;

the method further comprising:

via a positive displacement pump coupled to receive the fluid through the conduit from the diaphragm pump, controlling a flow of the fluid through the conduit and the positive displacement pump to a recipient; and controlling the positive displacement pump to deliver the fluid to the recipient based on feedback indicating a rate at which the diaphragm pump delivers the fluid through the conduit to the positive displacement pump.

2. The method as in claim 1 further comprising:
controlling flow of the fluid from the chamber to the recipient via a valve disposed downstream of the diaphragm pump.

3. The method as in claim 1 further comprising:
controlling a flow of fluid from different fluid sources into the chamber of the diaphragm pump.

4. The method as in claim 1 further comprising:
via an air elimination filter disposed in the conduit between the diaphragm pump and the positive displacement pump, removing gas from the fluid.

5. The method as in claim 4 further comprising:
controlling a rate of fluid flowing through the diaphragm pump via operation of the positive displacement pump.

6. The method as in claim 1 further comprising:
calculating a flow rate of delivering the fluid from the chamber through the conduit based on calculated amounts of fluid in the chamber at multiple different times during a delivery phase.

7. The method as in claim 1 further comprising:
via the positive displacement pump coupled to receive the fluid from the conduit, blocking a flow of the fluid from the conduit to the recipient.

8. The method as in claim 1 further comprising:
controlling delivery of fluid from the positive displacement pump to the recipient at a flow rate as specified by a flow rate setting.

9. A fluid delivery system comprising:
a controller operative to:
apply a drive pressure to fluid in a chamber of a diaphragm pump, the applied drive pressure causing flow of the fluid out of the chamber in a downstream direction from the diaphragm pump through a conduit;
temporarily discontinue application of the drive pressure to the chamber for a time duration;
calculate a portion of the fluid remaining in the chamber based on measurements obtained during the time duration; and
subsequent to the time duration, resume application of the drive pressure to the chamber, the resumed application of drive pressure causing resumed flow of the remaining fluid out of the chamber and through the conduit;
the fluid delivery system further comprising: a positive displacement pump coupled to receive the fluid from the conduit, the positive displacement pump operative to control a flow rate of the fluid through the conduit and the positive displacement pump to a recipient; and
wherein the controller is further operative to: control the flow of fluid from the positive displacement pump based on feedback indicating a rate at which the diaphragm pump delivers the fluid through the conduit.

10. The fluid delivery system as in claim 9, wherein the controller is further operative to:
control flow of the fluid from the chamber to the recipient via a valve disposed downstream of the diaphragm pump.

11. The fluid delivery system as in claim 9, wherein the controller is further operative to:
control a flow of fluid from different fluid sources into the chamber of the diaphragm pump.

12. The fluid delivery system as in claim 9 further comprising:
an air elimination filter disposed in the conduit between the diaphragm pump and the positive displacement pump, the air elimination filter operative to remove gas from the flowing fluid.

13. The fluid delivery system as in claim 12, wherein the controller is further operative to:
control a rate of fluid flowing through the diaphragm pump via operation of the positive displacement pump.

14. The fluid delivery system as in claim 9, wherein the controller is further operative to:
calculate a flow rate of delivering the fluid from the chamber through the conduit based on calculated amounts of fluid in the chamber at multiple different times during a delivery phase.

15. The fluid delivery system as in claim 9,
wherein the positive displacement pump is operative to block a flow of the fluid from the conduit to the recipient.

16. The fluid delivery system as in claim 9, wherein the controller is further operative to:
control delivery of fluid from the positive displacement pump to the recipient at a flow rate as specified by a flow rate setting.

17. Computer-readable hardware storage having instructions stored thereon, the instructions, when executed by computer processor hardware, cause the computer processor hardware to:
apply a drive pressure to fluid in a chamber of a diaphragm pump, the applied drive pressure causing flow of the fluid out of the chamber in a downstream direction from the diaphragm pump through a conduit;
temporarily discontinue application of the drive pressure to the chamber;
during the temporary discontinued application of the drive pressure, calculate a portion of the fluid remaining in the chamber;
resume application of the drive pressure to the chamber, the resumed application of drive pressure causing resumed flow of the remaining fluid out of the chamber and through the conduit;
via a positive displacement pump coupled to receive the fluid through the conduit from the diaphragm pump, control a flow of the fluid through the conduit and the positive displacement pump to a recipient; and
control the positive displacement pump to deliver the fluid to the recipient based on feedback indicating a rate at which the diaphragm pump delivers the fluid through the conduit to the positive displacement pump.

18. The method as in claim 1 further comprising:
controlling multiple valves upstream of the diaphragm pump, control of a first valve of the multiple valves controlling input of a first fluid into the diaphragm pump, control of a second valve of the multiple valves controlling input of a second fluid into the diaphragm pump.

19. The method as in claim 1, wherein temporarily discontinuing application of the drive pressure to the chamber causes pumping of the fluid from the chamber through the conduit to substantially stop.

20. The method as in claim 1, wherein the diaphragm pump is a first fluid pump; and wherein resuming application of the drive pressure to the chamber causes continued flow of the remaining portion of fluid in the chamber downstream through the conduit to the positive displacement pump.

21. The method as in claim 1, wherein applying the drive pressure to the chamber includes:

applying a substantially constant pressure to the chamber to evacuate the fluid from the chamber into the conduit that conveys the fluid to the recipient.

22. The method as in claim 1, wherein discontinuing application of the pressure to the chamber causes a pumping of the fluid in the chamber through the conduit to substantially stop.

23. The method as in claim 1, wherein the drive pressure is temporarily discontinued in a window of time of a pump cycle, the window of time falling between a first event of filling the chamber with the fluid and a second event of refilling the chamber with additional fluid.

24. The method as in claim 23 further comprising:

at a beginning of the window of time, temporarily discontinuing application of the drive pressure to the chamber; and at an end of the window of time, resuming application of the drive pressure to the chamber.

25. The method as in claim 1 further comprising:

at multiple different times during a delivery cycle, temporarily discontinuing application of the pressure to the chamber to calculate an amount of the fluid remaining in the chamber;

the method further comprising:

calculating a flow rate of delivering the fluid in the chamber through the conduit based on the calculated amount of fluid in the chamber at the multiple different times during the delivery phase.

26. The method as in claim 25 further comprising:

at a beginning of the delivery cycle, filling the chamber with the fluid; and at an end of the delivery cycle, refilling the chamber with fluid.

27. The method as in claim 1 further comprising:

at a beginning of a delivery cycle, filling the chamber with the fluid;

at an end of the delivery cycle, refilling the chamber with additional fluid; and temporarily discontinuing and resuming application of the drive pressure to the chamber in between the beginning of the delivery cycle and the end of the delivery cycle.

28. The method as in claim 1 further comprising:

measuring a first remaining portion of fluid in the chamber in a first window of time during which the drive pressure is temporarily discontinued in a fluid delivery cycle; and measuring a second remaining portion of fluid in the chamber in a second window of time during which the drive pressure is temporarily discontinued in the fluid delivery cycle.

\* \* \* \* \*